US008865230B2

(12) United States Patent
Enan

(10) Patent No.: US 8,865,230 B2
(45) Date of Patent: Oct. 21, 2014

(54) COMPOSITIONS AND METHODS FOR TREATING PARASITIC INFECTIONS

(75) Inventor: Essam Enan, Davis, CA (US)

(73) Assignee: TyraTech, Inc., Melbourne, FL (US)

( * ) Notice: Subject to any disclaimer, the term of this patent is extended or adjusted under 35 U.S.C. 154(b) by 238 days.

(21) Appl. No.: 13/592,127

(22) Filed: Aug. 22, 2012

(65) Prior Publication Data

US 2012/0316248 A1 Dec. 13, 2012

Related U.S. Application Data

(62) Division of application No. 11/769,654, filed on Jun. 27, 2007, now abandoned.

(60) Provisional application No. 60/805,963, filed on Jun. 27, 2006, provisional application No. 60/822,067, filed on Aug. 10, 2006, provisional application No. 60/891,813, filed on Feb. 27, 2007, provisional application No. 60/865,109, filed on Nov. 9, 2006.

(51) Int. Cl.
*A01N 65/00* (2009.01)
*A61K 31/05* (2006.01)
*A61K 31/085* (2006.01)

(52) U.S. Cl.
CPC ............... *A61K 31/05* (2013.01); *A61K 31/085* (2013.01)
USPC .......................................................... 424/725

(58) Field of Classification Search
None
See application file for complete search history.

(56) References Cited

U.S. PATENT DOCUMENTS

| | | | |
|---|---|---|---|
| 3,943,063 A | 3/1976 | Morishita et al. |
| 3,971,852 A | 7/1976 | Brenner et al. |
| 4,211,668 A | 7/1980 | Tate |
| 4,278,658 A | 7/1981 | Hooper et al. |
| 4,320,113 A | 3/1982 | Kydonieus |
| 4,434,181 A | 2/1984 | Marks et al. |
| 4,551,480 A | 11/1985 | Stiefel et al. |
| 4,678,775 A | 7/1987 | Nathanson |
| 4,693,890 A | 9/1987 | Wilson et al. |
| 4,696,676 A | 9/1987 | Wilson et al. |
| 4,748,860 A | 6/1988 | Butler et al. |
| 4,759,228 A | 7/1988 | Butler et al. |
| 4,762,718 A | 8/1988 | Marks, Sr. |
| 4,764,367 A | 8/1988 | Wilson et al. |
| 4,783,457 A | 11/1988 | Nathanson |
| 4,801,446 A | 1/1989 | Wilson et al. |
| 4,801,448 A | 1/1989 | Wilson et al. |
| 4,808,403 A | 2/1989 | Wilson et al. |
| 4,816,248 A | 3/1989 | Wilson et al. |
| 4,818,526 A | 4/1989 | Wilson et al. |
| 4,859,463 A | 8/1989 | Wilson et al. |
| 4,876,087 A | 10/1989 | Wilson et al. |
| 4,880,625 A | 11/1989 | Wilson et al. |
| 4,885,855 A | 12/1989 | Marks et al. |
| 4,886,662 A | 12/1989 | Wilson et al. |
| 4,892,871 A | 1/1990 | Nathanson |
| 4,902,504 A | 2/1990 | Wilson et al. |
| 4,902,690 A | 2/1990 | Nathanson |
| 4,911,906 A | 3/1990 | Wilson et al. |
| 4,943,435 A | 7/1990 | Baker et al. |
| 4,959,209 A | 9/1990 | Wilson et al. |
| 4,970,068 A | 11/1990 | Wilson et al. |
| 4,988,507 A | 1/1991 | Wilson et al. |
| 4,988,508 A | 1/1991 | Wilson et al. |
| 4,988,509 A | 1/1991 | Wilson et al. |
| 4,990,684 A | 2/1991 | Hoelderich et al. |
| 4,992,270 A | 2/1991 | Wilson et al. |
| 5,091,423 A | 2/1992 | Wilson et al. |
| 5,110,594 A | 5/1992 | Morita |
| 5,118,711 A | 6/1992 | Wilson et al. |
| 5,126,369 A | 6/1992 | Wilson et al. |
| 5,134,892 A | 8/1992 | Wilson et al. |
| 5,165,926 A | 11/1992 | Wilson et al. |
| 5,175,175 A | 12/1992 | Wilson et al. |
| 5,190,745 A | 3/1993 | Dohara et al. |
| 5,196,200 A | 3/1993 | Wilson et al. |
| 5,204,372 A | 4/1993 | Wilson et al. |
| 5,205,065 A | 4/1993 | Wilson et al. |
| 5,228,233 A | 7/1993 | Butler et al. |
| 5,250,575 A | 10/1993 | Wilson et al. |
| 5,272,179 A | 12/1993 | Butler et al. |
| 5,281,621 A | 1/1994 | Wilson et al. |
| 5,321,048 A | 6/1994 | Wilson et al. |
| 5,327,675 A | 7/1994 | Butler et al. |
| 5,344,776 A | 9/1994 | Venter et al. |
| 5,344,847 A | 9/1994 | Wilson et al. |
| 5,354,783 A | 10/1994 | Marin et al. |
| 5,366,975 A | 11/1994 | Nathanson |
| 5,387,418 A | 2/1995 | Marin et al. |

(Continued)

FOREIGN PATENT DOCUMENTS

| | | |
|---|---|---|
| AU | 2004/201268 A1 | 4/2004 |
| CN | 1122703 A | 5/1996 |
| CN | 1481849 A | 3/2004 |
| JP | H1-301607 A | 12/1989 |
| JP | H2-207004 A | 8/1990 |

(Continued)

OTHER PUBLICATIONS

Hajhashemi, V., et al, "Black Cumin Seed Essential Oil, as a Potent Analgesic and Antiinflammatory Drug," Phytotherapy Research, 2004, 18:195-199.

(Continued)

*Primary Examiner* — Michael Meller

(74) *Attorney, Agent, or Firm* — Davis Wright Tremaine LLP

(57) ABSTRACT

Compositions for treating parasitic infections and methods of using the compositions to treat subjects with parasitic infections are provided. Methods of selecting compositions for use in treating parasitic infections are further provided.

7 Claims, 5 Drawing Sheets

(56) References Cited

U.S. PATENT DOCUMENTS

| | | | |
|---|---|---|---|
| 5,401,500 | A | 3/1995 | Warren et al. |
| 5,407,609 | A | 4/1995 | Tice et al. |
| 5,409,958 | A | 4/1995 | Butler et al. |
| 5,417,009 | A | 5/1995 | Butler et al. |
| 5,418,010 | A | 5/1995 | Janda et al. |
| 5,439,690 | A | 8/1995 | Knight et al. |
| 5,439,941 | A | 8/1995 | Butler et al. |
| 5,441,988 | A | 8/1995 | Butler et al. |
| 5,447,714 | A | 9/1995 | Marin et al. |
| 5,449,695 | A | 9/1995 | Marin et al. |
| 5,458,882 | A | 10/1995 | Marin et al. |
| 5,464,626 | A | 11/1995 | Warren et al. |
| 5,472,701 | A | 12/1995 | Warren et al. |
| 5,474,898 | A | 12/1995 | Venter et al. |
| 5,521,165 | A | 5/1996 | Warren et al. |
| 5,576,010 | A | 11/1996 | Warren et al. |
| 5,576,011 | A | 11/1996 | Butler et al. |
| 5,593,600 | A | 1/1997 | Solomon |
| 5,633,236 | A | 5/1997 | Warren et al. |
| 5,635,173 | A | 6/1997 | Warren et al. |
| 5,635,174 | A | 6/1997 | Warren et al. |
| 5,665,781 | A | 9/1997 | Warren et al. |
| 5,683,687 | A | 11/1997 | Marin et al. |
| 5,693,344 | A | 12/1997 | Knight et al. |
| 5,703,104 | A | 12/1997 | Peck et al. |
| 5,753,686 | A | 5/1998 | Marin et al. |
| 5,772,983 | A | 6/1998 | O'Connell et al. |
| 5,785,982 | A | 7/1998 | Warren et al. |
| 5,814,325 | A | 9/1998 | Rod |
| 5,827,584 | A | 10/1998 | Akao et al. |
| 5,840,669 | A | 11/1998 | Neelakantan |
| 5,849,317 | A | 12/1998 | Shorey et al. |
| 5,855,903 | A | 1/1999 | Warren et al. |
| 5,942,214 | A | 8/1999 | Lucas et al. |
| 5,956,865 | A | 9/1999 | Durance |
| 5,980,931 | A | 11/1999 | Fowler et al. |
| 5,990,178 | A | 11/1999 | Ninkov |
| 5,998,484 | A | 12/1999 | Zobitne et al. |
| 6,001,874 | A | 12/1999 | Veierov |
| 6,004,569 | A | 12/1999 | Bessette et al. |
| 6,006,470 | A | 12/1999 | Geoghegan et al. |
| 6,024,874 | A | 2/2000 | Lott |
| 6,114,384 | A | 9/2000 | Bessette et al. |
| 6,130,253 | A | 10/2000 | Franklin et al. |
| 6,143,288 | A | 11/2000 | Warren et al. |
| 6,183,767 | B1 | 2/2001 | Bessette et al. |
| 6,238,682 | B1 | 5/2001 | Klofta et al. |
| 6,255,356 | B1 | 7/2001 | Butler |
| 6,272,790 | B1 | 8/2001 | Paganessi et al. |
| 6,322,825 | B1 | 11/2001 | Ninkov |
| 6,329,433 | B1 | 12/2001 | Bessette et al. |
| 6,331,572 | B1 | 12/2001 | Bessette et al. |
| 6,333,302 | B1 | 12/2001 | Beer et al. |
| 6,333,360 | B1 | 12/2001 | Bessette et al. |
| 6,340,710 | B1 | 1/2002 | Bessette et al. |
| 6,342,535 | B1 | 1/2002 | Bessette et al. |
| 6,342,536 | B1 | 1/2002 | Bessette et al. |
| 6,360,477 | B1 | 3/2002 | Flashinski et al. |
| 6,368,508 | B1 | 4/2002 | Gatz et al. |
| 6,372,431 | B1 | 4/2002 | Cunningham et al. |
| 6,372,801 | B1 | 4/2002 | Bessette et al. |
| 6,372,803 | B1 | 4/2002 | Bessette et al. |
| 6,376,556 | B1 | 4/2002 | Bessette et al. |
| 6,395,789 | B1 | 5/2002 | Bessette et al. |
| 6,414,036 | B1 | 7/2002 | Ninkov |
| 6,451,844 | B1 | 9/2002 | Watkins et al. |
| 6,506,707 | B1 | 1/2003 | Bessette |
| 6,531,163 | B1 | 3/2003 | Bessette et al. |
| 6,534,099 | B1 | 3/2003 | Bessette et al. |
| 6,548,085 | B1 | 4/2003 | Zobitne et al. |
| 6,555,121 | B1 | 4/2003 | Bessette et al. |
| 6,610,254 | B1 | 8/2003 | Furner et al. |
| 6,649,660 | B2 | 11/2003 | Ninkov |
| 6,660,288 | B1 | 12/2003 | Behan et al. |
| 6,670,311 | B1 | 12/2003 | Aldcroft et al. |
| 6,689,395 | B2 | 2/2004 | Bessette |
| 6,713,518 | B1 | 3/2004 | Bessette et al. |
| 6,812,258 | B2 | 11/2004 | Bessette et al. |
| 6,841,577 | B2 | 1/2005 | Bessette et al. |
| 6,844,369 | B2 | 1/2005 | Ninkov |
| 6,849,614 | B1 | 2/2005 | Bessette et al. |
| 6,858,653 | B2 | 2/2005 | Bessette |
| 6,884,763 | B2 | 4/2005 | Willard |
| 6,887,899 | B1 | 5/2005 | Bessette |
| 6,921,539 | B2 | 7/2005 | Ninkov |
| 6,949,587 | B1 | 9/2005 | Bessette |
| 6,969,522 | B2 | 11/2005 | Bessette |
| 6,974,584 | B2 | 12/2005 | Bessette |
| 6,986,898 | B1 | 1/2006 | Bessette |
| 7,008,649 | B2 | 3/2006 | Bessette et al. |
| 7,109,240 | B2 | 9/2006 | Bessette et al. |
| 7,157,411 | B2 | 1/2007 | Rohde et al. |
| 7,201,926 | B2 | 4/2007 | Fried et al. |
| 7,208,519 | B2 | 4/2007 | Ninkov |
| 7,238,726 | B2 | 7/2007 | Bessette |
| 7,238,798 | B2 | 7/2007 | Lee et al. |
| 7,241,806 | B2 | 7/2007 | Bessette |
| 7,250,175 | B2 | 7/2007 | Bessette et al. |
| 7,291,650 | B2 | 11/2007 | Bessette et al. |
| 7,320,966 | B2 | 1/2008 | Bessette et al. |
| 7,351,420 | B2 | 4/2008 | Bessette et al. |
| 7,357,939 | B2 | 4/2008 | Bessette |
| 7,361,366 | B2 | 4/2008 | Bessette et al. |
| 7,381,431 | B2 | 6/2008 | Baker et al. |
| 7,541,155 | B2 | 6/2009 | Enan |
| 7,622,269 | B2 | 11/2009 | Enan |
| 7,892,581 | B2 | 2/2011 | Kvitnitsky |
| 2002/0028256 | A1 | 3/2002 | Bessette |
| 2002/0034556 | A1 | 3/2002 | Khazan |
| 2002/0073928 | A1 | 6/2002 | Ingman et al. |
| 2002/0076360 | A1 | 6/2002 | Ingman et al. |
| 2002/0081230 | A1 | 6/2002 | Ingman et al. |
| 2002/0096121 | A1 | 7/2002 | Ingman et al. |
| 2002/0107287 | A1 | 8/2002 | Bessette et al. |
| 2003/0026823 | A1 | 2/2003 | Fried et al. |
| 2003/0036530 | A1 | 2/2003 | Bessette |
| 2003/0039674 | A1 | 2/2003 | Bessette |
| 2003/0083212 | A1 | 5/2003 | Willard |
| 2003/0091531 | A1 | 5/2003 | Kensek |
| 2003/0091657 | A1 | 5/2003 | Chiasson |
| 2003/0091661 | A1 | 5/2003 | Bessette |
| 2003/0108622 | A1 | 6/2003 | Bessette et al. |
| 2003/0108623 | A1 | 6/2003 | Bessette et al. |
| 2003/0175369 | A1 | 9/2003 | Khazan-Enache |
| 2003/0194454 | A1 | 10/2003 | Bessette et al. |
| 2003/0231978 | A1 | 12/2003 | Franklin et al. |
| 2004/0146595 | A1 | 7/2004 | Bessette et al. |
| 2004/0156922 | A1 | 8/2004 | Bessette et al. |
| 2004/0185080 | A1 | 9/2004 | Hojo et al. |
| 2004/0192551 | A1 | 9/2004 | Bessette |
| 2004/0213822 | A1 | 10/2004 | Birch et al. |
| 2004/0248791 | A1 | 12/2004 | Spana et al. |
| 2005/0004233 | A1 | 1/2005 | Bessette et al. |
| 2005/0008714 | A1 | 1/2005 | Enan |
| 2005/0013885 | A1 | 1/2005 | Chiasson |
| 2005/0019269 | A1 | 1/2005 | Marks et al. |
| 2005/0070576 | A1 | 3/2005 | Spooner-Hart et al. |
| 2005/0136089 | A1 | 6/2005 | Bessette et al. |
| 2005/0143260 | A1 | 6/2005 | Bessette et al. |
| 2005/0147636 | A1 | 7/2005 | Bessette et al. |
| 2005/0163869 | A1 | 7/2005 | Bessette et al. |
| 2005/0170024 | A1 | 8/2005 | Bessette et al. |
| 2005/0170025 | A1 | 8/2005 | Bessette et al. |
| 2005/0170026 | A1 | 8/2005 | Bessette et al. |
| 2005/0176117 | A1 | 8/2005 | Russell et al. |
| 2005/0214267 | A1 | 9/2005 | Enan |
| 2005/0260241 | A1 | 11/2005 | Bessette et al. |
| 2005/0260242 | A1 | 11/2005 | Bessette et al. |
| 2005/0288227 | A1 | 12/2005 | Marks et al. |
| 2006/0083763 | A1 | 4/2006 | Neale et al. |
| 2006/0088564 | A1 | 4/2006 | Bessette |
| 2006/0115507 | A1 | 6/2006 | Bessette |
| 2006/0115508 | A1 | 6/2006 | Bessette |
| 2006/0115509 | A1 | 6/2006 | Bessette |

(56) References Cited

U.S. PATENT DOCUMENTS

| | | |
|---|---|---|
| 2006/0115510 A1 | 6/2006 | Bessette |
| 2006/0121074 A1 | 6/2006 | Bessette |
| 2006/0263403 A1 | 11/2006 | Enan |
| 2007/0009616 A1 | 1/2007 | Marks |
| 2007/0098750 A1 | 5/2007 | Bessette |
| 2007/0178128 A1 | 8/2007 | Bessette |
| 2007/0190094 A1 | 8/2007 | Bessette |
| 2007/0207221 A1 | 9/2007 | Bessette et al. |
| 2007/0298131 A1 | 12/2007 | Bessette et al. |
| 2007/0299037 A1 | 12/2007 | Bessette et al. |
| 2007/0299038 A1 | 12/2007 | Bessette et al. |
| 2008/0003315 A1 | 1/2008 | Bessette et al. |
| 2008/0003316 A1 | 1/2008 | Bessette et al. |
| 2008/0003317 A1 | 1/2008 | Bessette et al. |
| 2008/0004240 A1 | 1/2008 | Bessette et al. |
| 2008/0015167 A1 | 1/2008 | Bessette et al. |
| 2008/0015249 A1 | 1/2008 | Bessette et al. |
| 2008/0020381 A1 | 1/2008 | Henrich et al. |
| 2008/0032387 A1 | 2/2008 | Bailey et al. |
| 2008/0038383 A1 | 2/2008 | Bessette et al. |
| 2008/0075796 A1 | 3/2008 | Enan |
| 2008/0131533 A1 | 6/2008 | Kvitnitsky et al. |
| 2008/0153904 A1 | 6/2008 | Bessette et al. |
| 2009/0232918 A1 | 9/2009 | Enan |
| 2011/0217397 A1 | 9/2011 | Enan |

FOREIGN PATENT DOCUMENTS

| | | |
|---|---|---|
| JP | H3-7210 A | 1/1991 |
| JP | H3-285993 A | 12/1991 |
| JP | H5-208902 A | 8/1993 |
| JP | H6-345613 A | 12/1994 |
| JP | H9-500367 T | 1/1997 |
| JP | H9-227305 A | 9/1997 |
| JP | H10-152407 A | 6/1998 |
| JP | H11-171703 A | 6/1999 |
| JP | H11-279583 A | 10/1999 |
| JP | 2000-166399 A | 6/2000 |
| JP | 2000-513027 T | 10/2000 |
| JP | 2001-294505 A | 10/2001 |
| JP | 2001-519367 T | 10/2001 |
| JP | 2002-501007 T | 1/2002 |
| JP | 2002-173407 A | 6/2002 |
| JP | 2002-521406 T | 7/2002 |
| JP | 2003-505483 T | 2/2003 |
| JP | 2003-201203 A | 7/2003 |
| WO | WO 94/27434 A1 | 12/1994 |
| WO | WO 98/54971 A1 | 12/1998 |
| WO | WO 99/18802 A1 | 4/1999 |
| WO | WO 99/21891 A1 | 5/1999 |
| WO | WO 99/33973 A2 | 7/1999 |
| WO | WO 99/33973 A3 | 7/1999 |
| WO | WO 00/05964 A1 | 2/2000 |
| WO | WO 00/21364 A2 | 4/2000 |
| WO | WO 00/50566 A2 | 8/2000 |
| WO | WO 00/51436 A1 | 9/2000 |
| WO | WO 00/53020 A1 | 9/2000 |
| WO | WO 00/75322 A | 12/2000 |
| WO | WO 01/00020 A1 | 1/2001 |
| WO | WO 01/00026 A1 | 1/2001 |
| WO | WO 01/00032 A1 | 1/2001 |
| WO | WO 01/00033 A1 | 1/2001 |
| WO | WO 01/00034 A1 | 1/2001 |
| WO | WO 01/00049 A1 | 1/2001 |
| WO | WO 01/08496 A1 | 2/2001 |
| WO | WO 01/10214 A2 | 2/2001 |
| WO | WO 01/10214 A3 | 2/2001 |
| WO | WO 01/18201 A1 | 3/2001 |
| WO | WO 01/60163 A2 | 8/2001 |
| WO | WO 01/60163 A3 | 8/2001 |
| WO | WO 01/91554 A1 | 12/2001 |
| WO | WO 01/91556 A2 | 12/2001 |
| WO | WO 01/91556 A3 | 12/2001 |
| WO | WO 01/91560 A2 | 12/2001 |
| WO | WO 01/91560 A3 | 12/2001 |
| WO | WO 03/016477 A2 | 2/2003 |
| WO | WO 03/016477 A3 | 2/2003 |
| WO | WO 2004/006968 A1 | 1/2004 |
| WO | WO 2004/091307 | 10/2004 |
| WO | WO 2004/100971 A1 | 11/2004 |
| WO | WO 2005/070213 | 8/2005 |
| WO | WO 2005/092016 A2 | 10/2005 |
| WO | WO 2005/092016 A3 | 10/2005 |
| WO | WO 2008/003007 A2 | 1/2008 |
| WO | WO 2008/011054 A2 | 1/2008 |
| WO | WO 2008/003007 A3 | 5/2008 |

OTHER PUBLICATIONS

Özcan M., et al., "Aroma Profile of *Thymus vulgaris* L. Growing Wild in Turkey," Bulg. J. Plant Physiology, 2004. 30(3-4):68-73.

Peana, AT, et al., "Anti-inflammatory activity of linalool and linalyl acetate constituents of essential oils," Phytomedicine, 2000, 9(8):721-6 (abstract only).

Regnault-Roger, C., et al., "Insecticidal Effect of Essential Oils from Mediterranean Plants upon *Acanthoscelides obtectus* say (Coleoptera, Bruchidae), A Pest of Kidney Bean (*Phaseolus vulgaris* L.)," Journal of Chemical Ecology, 1993, 19(6):1233-1244.

Office Action, mailed in counterpart Indian Patent Application No. 10627/DELNP/2008, dated Apr. 24, 2014, 3 pgs.

Office Action (translation), mailed in counterpart Mexican Patent Application No. MX/a/2008/016453, dated Feb. 17, 2014, 7 pgs.

Rasooli, Iraj and Parviz, Owlia, "Chemoprevention by thyme oils of *Aspergillus parasiticus* growth and aflatoxin production," Phytochemistry, 2005, 66:2851-2856.

Office Action, mailed in related Mexican Patent Application No. MX/a/2008/016453, dated Jan. 23, 2013.

Abou El Ele, et al., *Bulletin of High Institute of Public Health*, University of Alexandria, Alexandria, Egypt. 31(1):15-30, 2001. "Insecticidal activity of some essential oils: cAMP mediates effect."

Alvarez-Sanchez, et al., *Microb Pathog.* 28(4):193-202, Apr. 2000, "A novel cysteine proteinase (CP65) of *Trichomonas vaginalis* involved in cytotoxicity."

Aoyama, et al., *Arch Insect Biochem Physiol.*, 47(1):1-7, May 2001. "Substituent-dependent, positive and negative modulation of *Bombyx mori* adenylate cyclase by synthetic octopamine/tyramine analogues."

Arakawa, et al., *Neuron.* 4(3):343-354, Mar. 1990. "Cloning, localization, and permanent expression of a *Drosophila* octopamine receptor."

Atayde, et al., *Infection and Immunity*, Jul. 2007, pp. 3264-3270. "Expression and Cellular Localization of Molecules of the gp82 Family in *Trypanosoma cruzi* Metacyclic Trypomastigtes."

Baxter, et al., *Insect Biochem Mol Biol.* 29(5):461-467, May 1999. "Isolation of a cDNA for an octopamine-like, G-protein coupled receptor from the cattle tick, *Boophilus mocroplus*."

Bekele, et al., "Blend effects in the toxicity of the essential oil constitutents of *Ocimum kilimandscharium* and *Ocimum kenyense* (Labiatae) on two post-harvest insect pests." *Medicinal & Aromatic Plants Abstracts Resources*, New Delhi, India—New Delhi, vol. 23, No. 6; Dec. 1, 2001.

Bhat et al., *The Journal of Biological Chemistry*, vol. 282, No. 48, pp. 34877-34887, Nov. 30, 2007. "Cryptosporidium p30, a Galactose/*N*-Acetylgalactosamine-specific Lectin. Mediates Infection in Vitro."

Bischof, et al., *Insect Biochem Mol Biol.* 34(6):511-521, Jun. 2004. "Cloniong, expression and functional anlaysis of an octopamine receptor from *Periplaneta americana*."

Blazquez, et al., *International Journal for Parasitology*, No. 37, 2007, pp. 425-433. "Initiation of inflammation and cell death during liver abscess formation by *Entamoeba histolytica* depends on activity of the galactose/*N*-acetyl-D-galactosamine lectin."

Blenau, et al., *J Neurochem.* 74(3):900-908, Mar. 2000. "Amtyrl: characterization of a gene from honeybee (*Apis mellifera*) brain encoding a functional tyramine receptor."

Blenau, et al., *Archives of Insect Biochemistry and Physiology*. 48(1): 13-38, Sep. 2001. "Molecular and Pharmacology Properties of Insect Biogenic Amine Receptors: Lessons from *Drosophila melanogastor* and *Apis mellifera*."

(56) References Cited

OTHER PUBLICATIONS

Borowsky, et al., *Proc Natl Acad Sci USA*. 98(16):8966-8971, Jul. 31, 2001. "Trace amines: Indentification of a family of mammalian G protein-coupled receptors."
Bradley et al., *Current Opinion in Microbiology*. Nov. 9, 2007, 10:582-587. "Rhoptries: an arsenal of secreted virulence factor."
Bunzow, et al., *Mol Pharmacol* 60(6):1181-1188, Dec. 2001. "Amphetamine, 3,4-Methylenedioxymethamphetamine, Lysergic Acid Diethylamide, and Metabolites of the Catecholamine Neurotransmitters Are Agonists of a Rat Trace Amine Receptor."
Chirgwin, et al., *Biochemistry* 18(24):5294-5299, Nov. 27, 1979. "Isolation of biologically active ribonucleic acid from sources einriched in ribonulcease."
Coats, *Environ Health Prespect*. 87:255-262, 1990. "Mechanisms of toxic action and structure-activity relationships for organochlorine and synthetic pyrethroid insecticides."
Coats, et al., *Naturally occurring pest bioregulators* (Hedina PA, ed), Amer. Chem. Soc., Washington, DC. Chapter 20, pp. 305-316, 1991. "Toxicity and neurotoxic effects of monoterpenoids in insects and earthworms."
Cooley L, et al., *Science*. 239(4844):1121-1128, Mar. 4, 1988. "Insertional mutagenesis of the *Drosophila* genome with single P elements."
Davids et al., *International Journal for Parsitology*, 38 (2008), pp. 353-369. *Giardia lamblia* aurora kinase: A regulation of mitosis in a binucleate parasite.
Donini, et al., *J Insect Physiol*. 50(4):351-361, Apr. 2004. "Evidence for a possible neurotransmitter/neuromodulator role of tyramine on the locust oviducts."
Downer, et al., *Neurochem Res*. 18(12):1245-1248, Dec. 1993. "Characterization of the tyraminergic system in the centrla nervous system of the locust, *Locusta* migratoria migratoides."
Downer, et al., *Insect Neurochemistry and Neurophysiology 1993* (Borkovec AB and Loeb MJ, eds), CRC Press, Boca Raton, Florida. pp. 23-38, 1994. "Biogenic amines in insects."
Dudai, et al., *J Neurochem*, 38(6):1551-1558, Jun. 1982. "Aminergic receptors in *Drosophila melanogaster*: properties of [3H]dihydroergocryptine binding sites."
Dyer, et al. *J Agric Food Chem*. 53(23):9281-9287, 2005. "Fusarium graminearum TRI14 is required for high virulence and DON production on wheat but not for DON synthesis in vitro."
Eichhorn et al. *The Plant Cell*. vol. 18, 3332-3345, Nov. 2006. "A Ferroxidation/Permeation Iron Uptake System Is Required for Virulence in *Ustilago maydis*."
Enan, et al., *Biochem Pharmacol*. 51(4):447-454, Feb. 23, 1996. "Deltamethrin induced thymus atrophy in male Balb/c mice."
Enan, et al., "Insecticidal action of terpenes and phenols to cockroaches: effect on octopamine recetors." International Symposium on Crop Protection, Ghent, Belgium; May 1998.
Enan, "Insecticidal activity of essential oils:L octopaminergic sites of action." *Comp. Biochem. Physiol. Part C: Toxicol. & Pharm., Elsevier*: 130(1): 325-337, Nov. 2001.
Enan, *Insect Biochem Mol Biol*. 35(4):309-321, 2005. "Molecular response of *Drosophila melanogaster* tyramine receptor cascade to plant essential oils."
EPA "R.E.D. Facts"; *Flowers and Vegetable Oils*, EPA-738-F-93-027 (Dec. 1993).
Erben et al., *Molecular & Biochemical Parasitology*, 153. Mar. 12, 2007, pp. 186-193.
Evans, et al., *Nature*. 287(57777):60-62, Sep. 4, 1980. "Action of formamidine pesticides on octopamine receptors."
Evans, *J Physiol*. 318:99-122, Sep. 1981. "Multiple receptor types for octopamine in the locust."
Evans, et al., *Prog Brain Res*. 106:259-268, 1999. "Agonist-specific coupling of G-protein-coupled receptors to second-messenger systems."
Finney, *Probit Analysis*, 3rd Ed., Cambridge Unviersity Press. London, p. 333, 1971.

Gerhardt, et al., *Mol Pharmacol*. 51(2):293-300, Feb. 1997. "Molecular cloning and pharmacological characterization of a molluscan octopamine receptor."
Griffin, et al., Eur. J. Pharmacol. 377:117-125, 1999.
Grodnitsky, et al., *J Agric Food Chem*. 50(16):4576-4580, Jul. 31, 2002. "QSAR evaluation fo monoterpenoids' insecticidal activity."
Grundy, et al., *Pestic Biochem Physiol*. 23(3):383-388, 1985. "Inhibiition of acetylcholinesterases by pulgeone-1,2-eopoxide."
Gudermann, et al., *Annu Rev Pharmacol Toxicol*. 36:429-459, Apr. 1996, "Diversity and selectivity of receptor-G protein interaction."
Gudermann, et al., *Annu Rev Neurosci*. 20:399-427, Mar. 1997. "Functional and structural complexity of signal transduction via G-protien-coupled receptors."
Guillen, et al., *Life Sci*. 45(7):655-662, 1989. "A possible new class of octopamine receptors coupled to adenylate cyclase in the brain of the dipterousl *Ceratitis capitata*. Pharmacological characterization and regulation of 3H-octopamine binding."
Han, et al., *Journal of Neuroscience*, 18(10): 3650-3658, May 15, 1998. "A Novel Octopamine Receptor with Preferential Expression in *Drosophilla* Mushroom Bodies."
Hayashi et al., "The scent substances of pierid butterflies hebomoiaglaucippe and the volatile components of their food plants crataevareligiose." *Zeitschrift Fuer Naturforschung Section C Journal of Biosciences*, vol. 40, No. 1-2, 1985, pp. 47-50.
Hernandez-Sanchez et al., "Attractiveness for *Ceratitis capita* (Wiedemann) (Dipt., Tephritidae) of mango (Mangifera indica, cv. Tommy Atkins) airborne terpenes," *Journal of Applied Entemology*, vol. 125, No. 4, May 2001, pp. 189-192.
Hiripi, et al., *Brain Res*. 633(1-2):119-126, 1994. "Characterization of tyramine and octopamine receptors in the insect (*Locusta migratoria migratoriodes*) brain."
Hori, *Appl Entomol Zool*. 34(3):351-358, 1999. "The effects of rosemary and ginger oils on the alighting behavior of *Myzus persicae* (Sulzer) (Homoptera: Aphididae) and on the incidnece of yellow spooted streak."
Hummelbrunner et al., "Acute, sublethal, anitfeedant, and synergistic effects of monoterpenoid essential oil compounds on the tobacco cutworm, *Spodoptera litura* (Lep., Noctuidae)," *Medicinal & Aromatic Plants Abstracts, Resource*. New Delhi, India—New Delhi, vol. 23, No. 4, Aug. 1, 2001.
James, et al., *J Chem Ecol*. 30(8):1613-1628, 2004. "Field-testing of methyl salicylate for recruitment and retenetion of beneficial insects in grapes and hops."
Janmaat et al., "Enhanced fumigant toxicity of—cymene against *Frankliniella occidentalis* by simultaneous application of elevated levels of carbon dioxide," *Pest Management Science, Wiley & Sons, Bonger Regis*, GB. vol. 58, Jan. 1, 2001, pp. 167-173.
Jurgens et al., "Floral scent compounds of Amazonian Annonaceae species pollinated by small beetles and thrips," *Photochemistry, Pergamon Press*, GB. vol. 55, No. 6, No. 1, 2000, pp. 551-558.
Karr, et al, *J Econ Entomol*. 85(2),424-429, 1992. "Effect of four monoterpenoids on growth and reproduction of the German cockroach (Blattodea: Blattellidae)."
Khan, et al., *Arch Insect Biochem Physiol*. 52(1):7-16, 2003. "Positive and negative modulation of *Bombyx mori* adenylate cyclase by 5-phenyloxazoles: identification of octopamine and tyramine receptor agonists."
Kostyukovsky, et al., *Pest Manag Sci*. 58(11):1101-1106, Nov. 2002. "Activation of octopaminergic recepotrs by essential oil constitutents isolated from aromatic plants: Possible mode of action against insect pests."
Kravitz, et al., *Neurosci Symp*. 1:67-81, 1976. "Octopamine neurons in lobsters."
Krymskaya, et al., "Mechanisms of Proliferation Synergy by Receptor Tyrosine Kinase and G Protein-Coupled Receptor Activation in Human Airway Smooth Muscle." *Am J Respir Cell Mol Biol*. 23(4):546-554.
Kutsukake, et al., "A tyramine receptor gene mutation causes a defective olfactory behavior in *Drosophila*." *Gene* 245:31-42, Mar. 7, 2000.
Kyte, et al., *J Mol Biol*. 157(1):105-132, 1982. "A simple method for displaying the hydropathic character of a protein."

(56) References Cited

OTHER PUBLICATIONS

Landolt, et al., *Environ Entomol.* 28(6):954-960, Dec. 1999. "Plant Essential Oils ans Arrestants and Repellents for Neonate Larvae of the Codling Moth (Lepidoptera: Tortricidae)."
Lee, et al., *J Econ Entomol.* 90(4):883-892, Aug. 1997. "Insecticidal activity of monoterpenoids to western corn rootworm (Coleoptera: Chrysomelidae), twospotted spider mite (Acari: Tetranychidae), and house fly (Diptera: Muscidae)."
Lee et al. "Fumigant Toxicity of Essential Oils and Nonoterpenes Against the Red Flour Beetle, *Tribolium castaneum* Herbst," *Journal of Asia Pacific Entomolgy, Korean Society of Applied Entomology*, Suwon, KR, vol. 5, No. 2, Nov. 1, 2002, pp. 237-240.
Lomasney, et al., *Proc Natl Acad Sci USA*. 87(13):5094-5098, Jul. 1990. "Expanison of the alpha 2-adrenergic receptor family: cloning and characterization of a human alpha 2-adrenergic receptor subtype, the gene for which is located on chromosome 2."
Lynn,et al., *Cytotechnology.* 20(2):3-11, Apr. 11, 1996. "Development and characterization of insect cell lines."
Lynn,et al., *J Insect Sci.* 2:9, May 20, 2002. "Methods for Maintaining Insect Cell Cultures."
McCaffery, et al., IRAC Symposium on Insecticide Sustainability: Neonicotinoids ESA Annual Meeting, Dec. 2005. "Effective resistance management for the neonicotinoids: Industry's approach to ensure the continued efficacy of a key insecticide class."
Macchioni, et al. J. Agric. Food. Chem. 50: 4586-4588, 2002.
Menevse, et al., *Biochem Biophys Res Com.* 77(2):671-677, 1977. "Evidence for the specific involvement of cyclic AMP in the olfactory transduction mechanism."
Michon, et al., *Mol Biol Evol.* 19(7):1128-1142, Jul. 2002. "Evolutionary relationships of conserved cysteine-rich motifs in adhesive molecules of malaria parasites."
Miyazawa, et al., *J Agric Food Chem.* 45(3):677-679, Mar. 1997. "Inhibition of Acetylcholinesterase Acitivity by Monoterpenoids with a p-Menthane Skeleton."
Morty, et al., *J Biol Chem.* 274(37):26149-26156, Sep. 10, 1999. "Oligopeptidase B from *Trypanosoma brucei*, a new member of an emeging subgroup of serine oligopeptidases."
Muller-Riebau, et al., *J Agric Food Chem.* 43:2262-2266, 1995. "Chemical Composition and Fungitoxic Properties to Phytopathogenic Fungei of Essential Oils of Selected Aromatic Plant Growing Wild in Turkey."
Mundodi, et al., Mol Microbiol. 53(4):1099-1108, 2004. "Silencing the ap65 gene reduces adherence to vaginal epithelial cells by *Trichomonas vaginalis*."
Ngoh, et al. *Pestic Sci.* 54(3):261-268, 1998. "Insecticidal and repellent properties of nine volatile constituents of essential oils against the American cockroach, *Periplaneta americana* (L.)."
Nok, et al., *Parasitol Res.* 89(4):302-307, Mar. 2003. "Characterization of sialidase from *Entamoaeba hystolitica* and possible pathogenic role in amebiasis."
Ntiamoah et al., "Identity and bioactivity of oviposition deterrents in pine oil for the onion maggot, *Delia antiqua*." *Entomologia Experiemtalis et Applicata*, vol. 79, No. 2, 1996, pp. 219-226.
Ohta, et al., *Insect Mol Biol.* 12(3):217-223, Jun. 2003. "B96Bom encodes a *Bombyx mori* tyramine receptor negatively coupled to adenylate cyclase."
Orchard, *Can J Zool.* 60:659-669, 1982. "Octopamine in insects: neurotransmitter, neurohormone, and neuromodulator."
PCT/ISA, "Written Opinion of the International Searching Authority," corresponding International Patent Application No. PCT/US2007/72292, mailed on Feb. 5, 2008, 6 pages.
PCT/IB, "International Preliminary Report on Patentabilty," corresponding Internationa Patent Application No. PCT/US2007/72292, mailed on Jan. 6, 2009, 8 pages.
Reale, et al., *Brain Res.* 769(2):309-320, 1997. "The expression of a cloned *Drosphila* octopamine/tyramine receptor in *Xenopus* oocytes."
Rex, et al., *J Neurochem.* 82(6):1352-1359, Sep. 2002. "Characterization of a tyramine receptor from *Caenorhabditis elegans*."

Rice, et al. (1993); Chapter 8: Structural requirements for Monoterpenoid Activity Against Insects, pp. 92-108; American Chemical Society (ACS) Symposium Series developed from a symposium sponsored by the Division of Agrochemicals at the 205th National Meeting of the American chemical society in Denver Colorado, P.A. Hedin (ed.), Mar. 28-Apr. 2, 1993.
Rice. et al., *J Econ Entomol.* 87(5):1172-1179, 1994. "Insecticidal properties on monoterpenoid derivatives to the house flv (Diptera: muscidae) and red flour beetle (Coleoptera: tenebrionidae)."
Robb, et al., "Agonist-specific coupling of a cloned *Drosophila* octapamine/tyramine receptor to multiple second messenger systems." *EMBO J.*, Mar. 15, 1994, 13:6; 1325-1330.
Robertson, et al., *Int Rev Neurobiol.* 19:173-224, 1976. "Octopamine and some related noncatecholic amines in invertebrate nervous systems."
Roeder, *Life Sci.* 50(1):21-28, 1992. "A new octopamine receptor class in locust nervous tissue, the octopamine 3 (OA3) receptor."
Roeder, *Comp Biochem Physiol.* Part C, 107(1):1-12, 1994. Biogenic amines and their receptors in insects.
Roeder, *Prog Neurobiol.* 59(5):533-561, Dec. 1999. "Octopamine in invertebrates."
Ryan, et al.,*J Chem Eco.* 14(10):1965-1975, Oct. 1988. "Plant-insect coevolution and inhibition of acetylcholinesterase."
Saudou, et al., "Cloning and characterization of a *Drosophila* tyramine receptor." *EMBO J.*, Nov. 1990; 9:11; 361-3617.
Sangwan, et al., *Pestic Sci*. 28(3):331-335, 1990. "Nematicidal activity of some essential plant oils."
Sawamura, et al., *J Agric Food Chem.* 47(12):4868-4872, Nov. 9, 1999. "Inhibitory Effects of Citrus Essential Oils and Their Components on the Formation of N-Nitrosodimethylamine."
Shulaev, et al., *Nature.* 385(6618):718-721, Feb. 20, 1997. "Airborne signalling by methyl salicylate in plant pathogen resistance."
Tsao, et al., "Monoterpenoids and their synthetic deravatives as leads for new insect-control agents." *American Chemical Society*; Chapter 28; 1995.
Urban, et al., *EMBO J.* 18(3):512-521, Feb. 1, 1999. "An ATP-driven efflux pump is a novel pathogenicity factor in rice blast disease."
Van Poyer, et al., *Insec Biochem Mol Biol.* 31(4-5):333-338, Mar. 15, 2001. "Phenolamine-dependent adenylyl cyclase activation in *Drosophila* schneider 2 cells."
Vanden Broeck, et al., *J Neurochem.* 64(6):2387-2395, Jun. 1995. "Characterization of a cloned locust tyramine receptor cDNA by functional expression in permanently transformed *Drosophila* S2 cells."
Vernier, et al., *Trends Pharmacol Sci.* 16(11):375-385, Nov. 1995. "An evolutionary view of drug-receptor interaction: the bioamine receptor family."
Voigt, et al., Plant J. 42(3):364-375, 2005. "A secreted lipase of *Fusarium gramminearum* is a virulence factor required for infection of cereals."
Von Nickisch-Rosenegk, et al., *Insect Biochem Mol Biol.* 26(8-9):817-827, Sep.-Oct. 1996. "Cloning of biogenic amine receptors from moths (*Bombyx mori* and *Heliothis virescens*)."
Wetzel et al., *PHAS* 98(16):9377-9380, Jul. 31, 2001.
Yu, *Parasitol Res.* 88(5):412-420, Feb. 6, 2002. "A common oocyst surface antigen of Cryptosporidium recognized by monoclonal antibodies."
Berntzen AK, et al., "In vitro Hatching of Oncosphere of Hymenolepidid Cestodes." *J Parasitol*, vol. 51, No. 2, Section 1, pp. 235-242, Apr. 1965.
Colby, S.R., "Calculating Synergistic and Antagonistic Responses of Herbicide Combinations," *Weeds*, 15(1):20-22, 1967.
Davis, "Drug treatment of Intestinal Helminthiasis." World Health Organization, Geneva, 1973.
International Serach Report of the International Searching Authority (mailed Feb. 5, 2008), 1 page in International Application No. PCT/US07/72292.
Ito A, "In vitro Oncospheral Agglutination Given by Immune Sera From Mice Infected and Rabbits Injected With Eggs of *Hymenolepis nana.*" *Parasitology*, 71(3):465-473, 1975.
Melvin and Brooke, "Laboratory Procedures For the Diagnosis of Intestinal Parasites." DHEW Publications No. (CDC) 76-828, Public Health Services, 1975.

(56) References Cited

OTHER PUBLICATIONS

Pearson RD, et al., "Praziquantel: A Major Advance in Anthelminthic Therapy." *Annals of Internal Medicine*, 99(2):195-198, 1983.

Rim J, "Treatment of *Hymenolepis nana* Infection." *Post-Graduate Doctor Journal*. Middle East Edition, 5:330-334, 1985.

Socialist Republic of Vietnam, National Office of Intellectual Property, "Notice of Result of Examination," corresponding Vietnamese Patent Application No. 1-2008-03134, mailed on Apr. 17, 2011, 2 pages.

China State Intellectual Property Office, "Office Action," corresponding chinese Patent Application No. 200780024130.7, mailed on Mar. 23, 2011, 3 pages (translation only.).

COMPOSITIONS AND METHODS FOR TREATING PARASITIC INFECTIONS

RELATED APPLICATIONS

The present application is a divisional application of U.S. patent application Ser. No. 11/769,654, filed on Jun. 27, 2007 now abandoned, entitled COMPOSITIONS AND METHODS FOR TREATING PARASITIC INFECTIONS, which claims the benefit of the filing date of U.S. Provisional Application Ser. Nos. 60/805,963 filed Jun. 27, 2006; 60/822,067 filed Aug. 10, 2006; 60/865,109 filed Nov. 9, 2006; and 60/891,813 filed Feb. 27, 2007.

TECHNICAL FIELD

The presently-disclosed subject matter relates to methods for treating parasitic infections and compositions useful for treating parasitic infections.

INTRODUCTION AND GENERAL CONSIDERATIONS

Parasitic infections of plants, humans, and other animals pose a worldwide problem. For example, more than 650 million people are at risk for gastrointestinal parasitic infection, and about 200 million are actually infected. Various conditions contribute to the development and spread of parasitic infections, including: poor sanitary conditions; low host resistance; population expansion; inadequate control of vectors and infection reservoirs; increased migration of vectors; and increased migration of hosts, e.g., worldwide travel due to military operation or tourism.

Such parasitic infections present an abundance of medical and social problems. For example, the infection in a host can undermine child development, educational achievement, reproductive health, and social and economic development. Indeed, some parasitic infections can cause morbidity and mortality. Notwithstanding the severe impact that parasitic infections can have, relatively few treatment options are available.

Available treatments for parasitic infections are limited, and treatments for some parasitic infections are non-existent. In the 1960s, niclosamide (also known as yomesan) was identified for use in treating certain helminthic parasitic infections; however, niclosamide has certain drawbacks. For example, in many cases a single dose of niclosamide does not provide a curative effect, rather, a relapse ensues because the compound has difficulty accessing cysticercoids buried deeply within the mucosal villi. As such, satisfactory results require an extended treatment with niclosamide for approximately 7 days. See e.g., Davis, Drug treatment of intestinal helminthiasis, World Health Organization (WHO), Geneva, 1973.

Another drug that has been used to treat helminthic parasitic infections is Praziquantel (2-(cyclohexylcarbonyl)-1,2,3,6,7,11b-hexahydro-4H-pyrazino(2,1-a)isoquinolin-4-one; also known as Biltracide). See Pearson and Gurrant, Praziquantel: a major advance in anthelminthic therapy. Annals of Internal Medicine, 99:195-198, 1983. Praziquantel can be administered in a single dose; however, treatment strategies making use of Praziquantel are at risk because of the possibility of the development of resistance to Praziquantel.

Accordingly, there remains a need in the art for non-harmful compositions that are effective for treating parasitic infections.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Disclosure of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes compositions and methods for treating parasitic infections, and methods of screening for and selecting compositions useful for treating a parasitic infection.

In some embodiments, the composition for treating a parasitic infection in a subject includes two or more compounds selected from: trans-anethole, para-cymene, linalool, alpha-pinene, and thymol.

In some embodiments, the composition includes two more compounds selected from: para-cymene, linalool, alpha-pinene, and thymol. In some embodiments, the composition includes three or more compounds selected from: para-cymene, linalool, alpha-pinene, and thymol. In some embodiments, the composition includes para-cymene, linalool, alpha-pinene, and thymol. In some embodiments, the composition further includes soy bean oil.

In some embodiments, the composition includes 25-35% by weight para-cymene, 1-10% by weight linalool, 1-10% by weight alpha-pinene, 35-45% by weight thymol, and 20-30% by weight soy bean oil. In some embodiments, the composition includes 28.39% by weight para-cymene, 6.6% by weight linalool, 3.8% by weight alpha-pinene, 37.2% by weight thymol, and 24% by weight soy bean oil.

In some embodiments, the composition includes 25-35% by volume para-cymene, 1-10% by volume linalool, 1-10% by volume alpha-pinene, 35-45% by volume thymol and 20-30% by volume soy bean oil. In some embodiments, the composition includes 30% by volume para-cymene, 7% by volume linalool, 4% by volume alpha-pinene, 35% by volume thymol, and 24% by volume soy bean oil.

In some embodiments, the composition includes three or more compounds selected from: trans-anethole, para-cymene, linalool, alpha-pinene, and thymol. In some embodiments, the composition includes four or more compounds selected from: trans-anethole, para-cymene, linalool, alpha-pinene, and thymol. In some embodiments, the composition includes trans-anethole, para-cymene, linalool, alpha-pinene, and thymol.

In some embodiments, the composition includes 15-25% by weight trans-anethole, 30-40% by weight para-cymene, 1-10% by weight linalool, 1-10% by weight alpha-pinene, and 35-45% by weight thymol. In some embodiments, the composition includes 18.2% by weight trans-anethole, 34.4% by weight para-cymene, 4.7% by weight linalool, 1.9% by weight alpha-pinene, and 40.8% by weight thymol.

In some embodiments, the composition includes 10-20% by volume trans-anethole, 30-40% by volume para-cymene, 1-10% by volume linalool, 1-10% by volume alpha-pinene, and 35-45% by volume thymol. In some embodiments, the composition includes 17% by volume trans-anethole, 37% by volume para-cymene, 5% by volume linalool, 2% by volume alpha-pinene, and 39% by volume thymol.

In some embodiments, the composition includes 15-25% by weight trans-anethole, 1-10% by weight para-cymene, 35-45% by weight linalool, 1-10% by weight alpha-pinene, and 30-40% by weight thymol. In some embodiments, the composition includes 18.2% by weight trans-anethole, 1.9% by weight para-cymene, 40.8% by weight linalool, 4.7% by weight alpha-pinene, and 34.4% by weight thymol.

In some embodiments, the composition includes 15-25% by volume trans-anethole, 1-10% by volume para-cymene, 35-45% by volume linalool, 1-10% by volume alpha-pinene, and 30-40% by volume thymol. In some embodiments, the composition includes 17% by volume trans-anethole, 2% by volume para-cymene, 39% by volume linalool, 5% by volume alpha-pinene, and 37% by volume thymol.

In some embodiments, the compounds of the composition together demonstrate a synergistic anti-parasitic effect. In some embodiments, the actual percent effect of the composition is greater than the expected percent effect of the composition. In some embodiments there is a coefficient of synergy relative to a component of the composition is greater than 5, 10, 25, 50, 75, or 100.

In some embodiments, the parasitic infection is by a protozoan parasite. In some embodiments, the parasite is selected from intestinal protozoa, tissue protozoa, and blood protozoa. In some embodiments, the parasite is selected from: *Entamoeba hystolytica, Giardia lamblia, Cryptosporidium muris, Trypanosomatida gambiense, Trypanosomatida rhodesiense, Trypanosomatida crusi, Leishmania mexicana, Leishmania braziliensis, Leishmania tropica, Leishmania donovani, Toxoplasma gondii, Plasmodium vivax, Plasmodium ovale, Plasmodium malariae, Plasmodium falciparum, Trichomonas vaginalis,* and *Histomonas meleagridis*.

In some embodiments, the parasitic infection is by a helminthic parasite. In some embodiments, the parasite is selected from nematodes. In some embodiments, the parasite is selected from Adenophorea. In some embodiments, the parasite is selected from Secementea. In some embodiments, the parasite is selected from: *Trichuris trichiura, Ascaris lumbricoides, Enterobius vermicularis, Ancylostoma duodenale, Necator americanus, Strongyloides stercoralis, Wuchereria bancrofti, Dracunculus medinensis*. In some embodiments, the parasite is selected from trematodes. In some embodiments, the parasite is selected from: blood flukes, liver flukes, intestinal flukes, and lung flukes. In some embodiments, the parasite is selected from: *Schistosoma mansoni, Schistosoma haematobium, Schistosoma japonicum, Fasciola hepatica, Fasciola gigantica, Heterophyes heterophyes, Paragonimus westermani*.

In some embodiments, the parasite is selected from cestodes. In some embodiments, the parasite is selected from *Taenia solium, Taenia saginata, Hymenolepis nana, Echinococcus granulosus*.

In some embodiments, the composition is provided in a formulation. The formulation can include the composition and a carrier, such as a food product. In some embodiments the formulation includes the composition encapsulated or microencapsulated with an outer shell material.

The presently-disclosed subject matter includes a method of treating a parasitic infection in a subject. In some embodiments, the method includes administering to the subject an effective amount of a composition as described herein.

The presently-disclosed subject matter includes a method for selecting a composition for use in treating a parasitic infection. In some embodiments, the method includes: providing a cell expressing a tyramine receptor; contacting test compounds to the cell; measuring the receptor binding affinity of the compounds; measuring at least one parameter selected from, (i) intracellular cAMP level, and (ii) intracellular $Ca^{2+}$ level; identifying a first compound for the composition that is capable of altering at least one of said parameters, and which has a high receptor binding affinity for the tyramine receptor; identifying a second compound for the composition that is capable of altering at least one of said parameters, and which has a low receptor binding affinity for the tyramine receptor; and selecting a composition including the first and second compounds. In some embodiments, the selected composition demonstrates an anti-parasitic effect that exceeds the anti-parasitic effect of any of the compounds when used alone.

DESCRIPTION OF EXEMPLARY EMBODIMENTS

Figure 1:
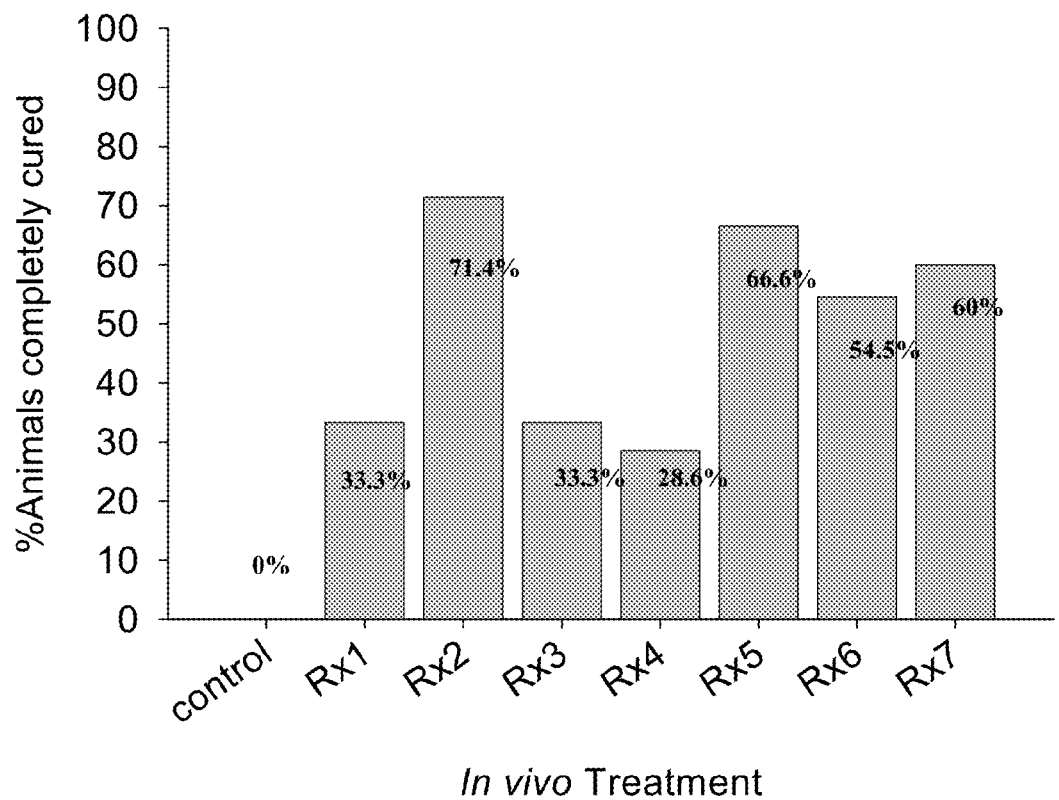
FIG. 1 is a bar graph demonstrating cure rates of animals infected with *H. nana* and treated with compounds disclosed herein.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes compositions and methods for treating parasitic infections, and methods of screening for and selecting compositions useful for treating a parasitic infection.

As used herein, the term "parasitic infection" refers to the infection of a plant or animal host by a parasite, such as a successful invasion of a host by an endoparasite, including for example a protozoan parasite or a helminthic parasite.

As used herein, the term "parasite" includes parasites, such as but not limited to, protozoa, including intestinal protozoa, tissue protozoa, and blood protozoa. Examples of intestinal protozoa include, but are not limited to: *Entamoeba hystolytica, Giardia lamblia,* and *Cryptosporidium muris*. Examples of tissue protozoa include, but are not limited to:

*Trypanosomatida gambiense, Trypanosomatida rhodesiense, Trypanosomatida crusi, Leishmania mexicana, Leishmania braziliensis, Leishmania tropica, Leishmania donovani, Toxoplasma gondii,* and *Trichomonas vaginalis.* Examples of blood protozoa include, but are not limited to *Plasmodium vivax, Plasmodium ovale, Plasmodium malariae,* and *Plasmodium falciparum. Histomonas meleagridis* is yet another example of a protozoan parasite.

As used herein, the term "parasite" further includes, but is not limited to: helminthes or parasitic worms, including nematodes (round worms) and platyhelminthes (flat worms). Examples of nematodes include, but are not limited to: animal and plant nematodes of the adenophorea class, such as the intestinal nematode *Trichuris trichiura* (whipworm) and the plant nematode *Trichodorus obtusus* (stubby-root nematode); intestinal nematodes of the secementea class, such as *Ascaris lumbricoides, Enterobius vermicularis* (pinworm), *Ancylostoma duodenale* (hookworm), *Necator americanus* (hookworm), and *Strongyloides stercoralis*; and tissue nematodes of the secementea class, such as *Wuchereria bancrofti* (Filaria bancrofti) and *Dracunculus medinensis* (Guinea worm). Examples of plathyeminthes include, but are not limited to: Trematodes (flukes), including blood flukes, such as *Schistosoma mansoni* (intestinal Schistosomiasis), *Schistosoma haematobium,* and *Schistosoma japonicum*; liver flukes, such as *Fasciola hepatica,* and *Fasciola gigantica*; intestinal flukes, such as *Heterophyes heterophyes*; and lung flukes such as *Paragonimus westermani.* Examples of platheminthes further include, but are not limited to: Cestodes (tapeworms), including *Taenia solium, Taenia saginata, Hymenolepis nana,* and *Echinococcus granulosus.*

Compositions of the presently-disclosed subject matter can be used to treat parasitic infections. In some embodiments, the compositions can include compounds that are generally regarded as safe (GRAS compounds). In some embodiments, the compositions can include compounds of a plant origin, such as plant essential oils or monoterpenoids of plant essential oils. In some embodiments, the compositions include two or more compounds. In some embodiments, the compositions can include any of the following oils, or mixtures thereof:

| | | | |
|---|---|---|---|
| t-anethole | corn oil | lilac flower oil (LFO) | piperonal |
| allyl sulfide | β-costol | lime oil | piperonyl |
| allyl trisulfide | cryptone | d-limonene | piperonyl acetate |
| allyl-disulfide | cumin oil | linalool | piperonyl alcohol |
| artemisia alcohol | curzerenone | linalyl acetate | piperonyl amine |
| acetate | p-cymene | linalyl anthranilate | prenal |
| benzaldehyde | davanone | lindestrene | pulegone |
| benzoic acid | diallyl tetrasulfide | lindenol | quinine |
| benzyl acetate | diethyl phthalate | linseed oil | rosemary oil |
| benzyl alcohol | dihydropyrocurzerenone | methyl-allyl-trisulfide | sabinene |
| bergamotene | | menthol | sabinyl acetate |
| β-bisabolene | dihydrotagentone | menthone | safflower oil |
| bisabolene oxide | beta-elemene | 2-methoxy | α-santalene |
| α-bisabolol | gamma-elemene | furanodiene | santalol |
| bisabolol oxide | Elmol | menthyl acetate | sativen |
| bisobolol oxide β | Estragole | methyl cinnamate | δ-selinene |
| bornyl acetate | 2-ethyl-2-hexen-1-ol | methyl citrate | sesame oil |
| β-bourbonene | eugenol | methyl di-hydrojasmonate | β-sesquphelandrene |
| black seed oil (BSO) | eugenol acetate | | silicone fluid |
| α-cadinol | α-farnesene | menthyl salicylate | sodium lauryl sulfate |
| camphene | (Z,E)-α-farnesene | mineral oil | soybean oil |
| α-campholene | E-β-farnesene | musk ambrette | spathulenol |
| α-campholene aldehyde | fenchone | myrcene | tagetone |
| camphor | furanodiene | myrtenal | tangerine oil |
| carvacrol | furanoeudesma-1,3-diene | neraldimethyl acetate | α-terpinene |
| d-carvone | | nerolidol | terpinene 900 |
| l-carvone | furanoeudesma-1,4-diene | nonanone | α-terpineol |
| caryophyllene oxide | | gamma-nonalactone | α-terpinolene |
| trans-caryophyllene | furano germacra 1,10(15)-diene-6-one | oil of pennyroyal | gamma-terpineol |
| castor oil | | olive oil | α-terpinyl acetate |
| cedar oil | furanosesquiterpene | orange sweet oil | 2-tert-butyl-p-quinone |
| chamazulene | garlic oil | 1-octanol | |
| 1,8-cineole | geraniol | E ocimenone | α-thujone |
| cinnamaldehyde | geraniol acetate | Z ocimenone | thyme oil |
| cinnamyl alcohol | germacrene D | 3-octanone | thymol |
| cinnamon oil | germacrene B | ocimene | thymyl methyl ether |
| citral A | grapefruit oil | octyl acetate | gamma-undecalactone |
| citral B | α-gurjunene | peanut oil | |
| isopropyl citrate | α-humulene | perillyl alcohol | valeric anhydride |
| citronellal | α-ionone | peppermint oil | vanillin |
| citronella oil | β-ionone | α-phellandrene | trans-verbenol |
| citronellol | isoborneol | β-phellandrene | cis-verbenol |
| citronellyl acetate | isofuranogermacrene | phenethyl proprionate | verbenone |
| citronellyl formate | iso-menthone | phenyl acetaldehyde | white mineral oil |
| clove oil | iso-pulegone | α-pinene | yomogi alcohol |
| α-copaene | jasmone | β-pinene | zingiberene |
| cornmint oil | lecithin | pine oil | |
| | lemon oil | trans-pinocarveol | |
| | lemon grass oil | | |

In some embodiments, compositions include two or more compounds selected from the following compounds:

| Compounds | CAS Registry No. |
|---|---|
| trans-anethole | 4180-23-8 |
| tert-butyl-p-benzoquinone | 3602-55-9 |
| black seed oil | 977017-84-7 |
| borneol | 507-70-0 |
| camphene | 79-92-5 |
| beta-caryophyllene | 87-44-5 |
| cineol | 470-82-6 |
| triethyl citrate | 77-93-0 |
| para-cymene | 99-87-6 |
| geraniol | 106-24-1 |
| hedion | 24851-98-7 |
| heliotropine | 120-57-0 |
| hercolyn D | 8050-15-5 |
| lilac flower oil | |
| lime oil | |
| d-limonene | 5989-27-5 |
| linalool | 78-70-6 |
| ethyl linalool | 10339-55-6 |
| tetrahydrolinalool | 78-69-3 |
| methyl salicylate | 119-36-8 |
| alpha-pinene | 80-56-8 |
| beta-Pinene | 127-91-3 |
| alpha-Terpinene | 99-86-5 |
| alpha-Thujene | 2867-05-2 |
| thyme oil | 8007-46-3 |
| thymol | 89-83-8 |
| wintergreen oil | 68-917-75-9 |

In some embodiments, compositions include two or more compounds selected from the following compounds:

| Compounds | CAS Registry No. |
|---|---|
| trans-anethole | 4180-23-8 |
| para-cymene | 99-87-6 |
| linalool | 78-70-6 |
| alpha-pinene | 80-56-8 |
| thymol | 89-83-8 |

In some embodiments of the compositions that include lilac flower oil, one or more of the following compounds can be substituted for the lilac flower oil: tetrahydrolinalool; ethyl linalool; heliotropine; hedion; hercolyn D; and triethyl citrate.

In some embodiments of the compositions that include black seed oil, one or more of the following compounds can be substituted for the black seed oil: alpha-thujene, α-pinene, β-pinene, p-cymene, limonene, and tert-butyl-p-benzoquinone.

In some embodiments of the compositions that include thyme oil, one or more of the following compounds can be substituted for the thyme oil: thymol, α-thujone; α-pinene, camphene, β-pinene, p-cymene, α-terpinene, linalool, borneol, and β-caryophyllene. In some embodiments of the compositions that include thymol, thyme oil can be substituted. In some embodiments of the compositions that include thyme oil, it can be desirable to include a specific type of thyme oil. In this regard, thyme oil (white) is preferred to thyme oil (red) because the latter has been found to cause negative side effects for the subject or host.

Compounds used to prepare embodiments of the compositions can be obtained, for example, from the following sources: Millennium Chemicals, Inc. (Jacksonville, Fla.), Ungerer Company (Lincoln Park, N.J.), SAFC (Milwaukee, Wis.), IFF Inc. (Hazlet, N.J.); Sigma Chemical Co. (St. Louis, Mo.); and The Lebermuth Company, Inc. (Southbend, Ind.).

In some embodiments of the compositions, it can be desirable to include a naturally-occurring version or a synthetic version of a compound. For example, in certain embodiments it can be desirable to include Lime Oil 410, a synthetic lime oil that can be obtained, for example, from Millennium Chemicals, Inc. In certain exemplary compositions, it can be desirable to include a compound that is designated as meeting Food Chemical Codex (FCC), for example, geraniol Fine FCC or Tetrahydrolinalool FCC, which compounds can be obtained, for example, from Millennium Chemicals, Inc.

In some embodiments of the compositions, it can be desirable to include a compound having a specific purity. In some embodiments of the compositions, it can be desirable to include compounds each having a purity of at least about 80%, 81%, 82%, 83%, 84%, 85%, 86%, 87%, 88%, 89%, 90%, 91%, 92%, 93%, 94%, 95%, 96%, 97%, 98%, or 99%. For example, in some embodiments of the compositions including alpha-pinene, an alpha-pinene that is at least about 98% pure can be selected. For another example, in embodiments of the compositions including linalool, a linalool that is at least about 97-99% pure (e.g., linalool coeur) can be selected.

In some embodiments of the compositions, it can be desirable to include compounds each having a purity of about 60%, 65%, 70%, 75%, 80%, 85%, 90%, or 95%. For example, in some embodiments of the compositions that include geraniol, it can be desirable to include a geraniol that is at least about 60%, 85% or 95% pure. In some embodiments, it can be desirable to include a specific type of geraniol. For example, in some embodiments, the compositions can include: geraniol 60, geraniol 85, or geraniol 95. When geraniol is obtained as geraniol 60, geraniol 85, or geraniol 95, then forty percent, fifteen percent, or five percent of the oil can be Nerol. Nerol is a monoterpene ($C_{10}H_{18}O$), which can be extracted from attar of roses, oil of orange blossoms and oil of lavender.

In some embodiments, compositions include two or more compounds selected from the following compounds: linalool, thymol, alpha-pinene, para-cymene, and trans-anethole. In some embodiments, compositions include three or more compounds selected from the following compounds: linalool, thymol, alpha-pinene, para-cymene, and Trans-Anethole. In some embodiments, compositions include four or more compounds selected from the following compounds: linalool, thymol, alpha-pinene, para-cymene, and Trans-Anethole. In some embodiments, compositions include: linalool, thymol, alpha-pinene, para-cymene, and Trans-Anethole. In some embodiments, it is preferred that an alpha-pinene that is at least about 98% pure is used. In some embodiments, it is preferred that a linalool that is a linalool coeur is used. In some embodiments, the composition can further include soy bean oil.

In some embodiments, compositions include two or more compounds selected from the following compounds: linalool, thymol, alpha-pinene, and para-cymene. In some embodiments, compositions include three or more compounds selected from the following compounds: linalool, thymol, alpha-pinene, and para-cymene. In some embodiments, compositions include: linalool, thymol, alpha-pinene, and para-cymene. In some embodiments, it is preferred that an alpha-pinene that is at least about 98% pure is used. In some embodiments, it is preferred that a linalool that is a linalool coeur is used. In some embodiments, the composition can further include soy bean oil.

In some embodiments, each compound can make up between about 1% to about 99%, by weight (wt/wt %) or by volume (vol/vol %), of the composition. For example, composition can comprises about 1% alpha-pinene and about 99% thymol. As used herein, % amounts, by weight or by volume, of compounds are to be understood as referring to relative amounts of the compounds. As such, for example, a composition including 7% linalool, 35% thymol, 4% alpha-pinene, 30% para-cymene, and 24% soy bean oil (vol/vol %) can be said to include a ratio of 7 to 35 to 4 to 30 to 24 linalool, thymol, alpha-pinene, para-cymene, and soy bean oil, respectively (by volume). As such, if one compound is removed from the composition, or additional compounds or other ingredients are added to the composition, it is contemplated that the remaining compounds can be provided in the same relative amounts. For example, if soy bean oil was removed from the exemplary composition, the resulting composition would include 7 to 35 to 4 to 40 linalool, thymol, alpha-pinene, and para-cymene, respectively (by volume). This resulting composition would include 9.21% linalool, 46.05% thymol, 5.26% alpha-pinene, and 39.48% para-cymene (vol/vol %). For another example, if safflower oil was added to the original composition to yield a final composition containing 40% (vol/vol) safflower oil, then the resulting composition would include 4.2% linalool, 21% thymol, 2.4% alpha-pinene, 18% para-cymene, 14.4% soy bean oil, and 40% safflower oil (vol/vol %).

In some embodiments, the composition includes about 1-5%, about 5-10%, about 10-15%, about 15-20%, about 20-25%, about 25-30%, about 30-35%, about 35-40%, about 40-45%, about 45-50%, about 50-60%, about 60-75%, or about 75-99% linalool, as measured by volume (vol/vol %). In some embodiments, the composition includes about 4.5-5.5% linalool, as measured by volume. In some embodiments, the composition includes about 5% linalool, as measured by volume. In some embodiments, the composition includes about 6.5-7.5% linalool, as measured by volume. In some embodiments, the composition includes about 7% linalool, as measured by volume. In some embodiments, the composition includes about 38-40% linalool, as measured by volume. In some embodiments, the composition includes about 39% linalool, as measured by volume.

In some embodiments, the composition includes about 1-5%, about 5-10%, about 10-15%, about 15-20%, about 20-25%, about 25-30%, about 30-35%, about 35-40%, about 40-45%, about 45-50%, about 50-60%, about 60-75%, or about 75-99% linalool, as measured by weight (wt/wt %). In some embodiments, the composition includes about 4.2-5.2% linalool, as measured by weight. In some embodiments, the composition includes about 4.7% linalool, as measured by weight. In some embodiments, the composition includes about 6.1-7.1% linalool, as measured by weight. In some embodiments, the composition includes about 6.6% linalool, as measured by weight. In some embodiments, the composition includes about 40.3-41.3% linalool, as measured by weight. In some embodiments, the composition includes about 40.8% linalool, as measured by weight.

In some embodiments, the composition includes about 1-5%, about 5-10%, about 10-15%, about 15-20%, about 20-25%, about 25-30%, about 30-35%, about 35-40%, about 40-45%, about 45-50%, about 50-60%, about 60-75%, or about 75-99% thymol, as measured by volume (vol/vol %). In some embodiments, the composition includes about 38-40% thymol, as measured by volume. In some embodiments, the composition includes about 39% thymol, as measured by volume. In some embodiments, the composition includes about 36-38% thymol, as measured by volume. In some embodiments, the composition includes about 37% thymol, as measured by volume. In some embodiments, the composition includes about 34-36% thymol, as measured by volume. In some embodiments, the composition includes about 35% thymol, as measured by volume.

In some embodiments, the composition includes about 1-5%, about 5-10%, about 10-15%, about 15-20%, about 20-25%, about 25-30%, about 30-35%, about 35-40%, about 40-45%, about 45-50%, about 50-60%, about 60-75%, or about 75-99% thymol, as measured by weight (wt/wt %). In some embodiments, the composition includes about 40.3-41.3% thymol, as measured by weight. In some embodiments, the composition includes about 40.8% thymol, as measured by weight. In some embodiments, the composition includes about 33.9-34.9% thymol, as measured by weight. In some embodiments, the composition includes about 34.4% thymol, as measured by weight. In some embodiments, the composition includes about 36.7-37.7% thymol, as measured by weight. In some embodiments, the composition includes about 37.2% thymol, as measured by weight.

In some embodiments, the composition includes about 1-5%, about 5-10%, about 10-15%, about 15-20%, about 20-25%, about 25-30%, about 30-35%, about 35-40%, about 40-45%, about 45-50%, about 50-60%, about 60-75%, or about 75-99% alpha-pinene, as measured by volume (vol/vol %). In some embodiments, the composition includes about 1.5-2.5% alpha-pinene, as measured by volume. In some embodiments, the composition includes about 2% alpha-pinene, as measured by volume. In some embodiments, the composition includes about 4.5-5.5% alpha-pinene, as measured by volume. In some embodiments, the composition includes about 5% alpha-pinene, as measured by volume. In some embodiments, the composition includes about 3.5-4.5% alpha-pinene, as measured by volume. In some embodiments, the composition includes about 4% alpha-pinene, as measured by volume.

In some embodiments, the composition includes about 1-5%, about 5-10%, about 10-15%, about 15-20%, about 20-25%, about 25-30%, about 30-35%, about 35-40%, about 40-45%, about 45-50%, about 50-60%, about 60-75%, or about 75-99% alpha-pinene, as measured by weight (wt/wt %). In some embodiments, the composition includes about 1.4-2.4% alpha-pinene, as measured by weight. In some embodiments, the composition includes about 1.9% alpha-pinene, as measured by weight. In some embodiments, the composition includes about 4.2-5.2% alpha-pinene, as measured by weight. In some embodiments, the composition includes about 4.7% alpha-pinene, as measured by weight. In some embodiments, the composition includes about 3.3-4.3% alpha-pinene, as measured by weight. In some embodiments, the composition includes about 3.8% alpha-pinene, as measured by weight.

In some embodiments, the composition includes about 1-5%, about 5-10%, about 10-15%, about 15-20%, about 20-25%, about 25-30%, about 30-35%, about 35-40%, about 40-45%, about 45-50%, about 50-60%, about 60-75%, or about 75-99% para-cymene, as measured by volume (vol/vol %). In some embodiments, the composition includes about 36.5-37.5% para-cymene, as measured by volume. In some embodiments, the composition includes about 37% para-cymene, as measured by volume. In some embodiments, the composition includes about 29.5-30.5% para-cymene, as measured by volume. In some embodiments, the composition includes about 30% para-cymene, as measured by volume. In some embodiments, the composition includes about 1.5-2.5% para-cymene, as measured by volume. In some embodiments, the composition includes about 2% para-cymene, as measured by volume.

In some embodiments, the composition includes about 1-5%, about 5-10%, about 10-15%, about 15-20%, about 20-25%, about 25-30%, about 30-35%, about 35-40%, about 40-45%, about 45-50%, about 50-60%, about 60-75%, or about 75-99% para-cymene, as measured by weight (wt/wt %). In some embodiments, the composition includes about 33.9-34.9% para-cymene, as measured by weight. In some embodiments, the composition includes about 34.4% para-cymene, as measured by weight. In some embodiments, the composition includes about 1.4-2.4% para-cymene, as measured by weight. In some embodiments, the composition includes about 1.9% para-cymene, as measured by weight. In some embodiments, the composition includes about 27.9-28.9% para-cymene, as measured by weight. In some embodiments, the composition includes about 28.4% para-cymene, as measured by weight.

In some embodiments, the composition includes about 1-5%, about 5-10%, about 10-15%, about 15-20%, about 20-25%, about 25-30%, about 30-35%, about 35-40%, about 40-45%, about 45-50%, about 50-60%, about 60-75%, or about 75-99% trans-anethole, as measured by volume (vol/vol %). In some embodiments, the composition includes about 16.5-17.5% trans-anethole, as measured by volume. In some embodiments, the composition includes about 17% trans-anethole, as measured by volume.

In some embodiments, the composition includes about 1-5%, about 5-10%, about 10-15%, about 15-20%, about 20-25%, about 25-30%, about 30-35%, about 35-40%, about 40-45%, about 45-50%, about 50-60%, about 60-75%, or about 75-99% trans-anethole, as measured by weight (wt/wt %). In some embodiments, the composition includes about 17.7-18.7% trans-anethole, as measured by weight. In some embodiments, the composition includes about 18.2% trans-anethole, as measured by weight.

In some embodiments, the composition includes the following compounds in the following relative amounts, where the relative amounts of the compounds are expressed as % wt/wt: 15-25% trans-anethole, 30-40% para-cymene, 1-10% linalool, 1-10% alpha-pinene, and 35-45% thymol. In some embodiments, the composition includes the following compounds in the following relative amounts, where the relative amounts of the compounds are expressed as % wt/wt: 18.2% trans-anethole, 34.4% para-cymene, 4.7% linalool, 1.9% alpha-pinene, and 40.8% thymol.

In some embodiments, the composition includes the following compounds in the following relative amounts, where the relative amounts of the compounds are expressed as % vol/vol: 10-20% trans-anethole, 30-40% para-cymene, 1-10% linalool, 1-10% alpha-pinene, and 35-45% thymol. In some embodiments, the composition includes the following compounds in the following relative amounts, where the relative amounts of the compounds are expressed as vol/vol: 17% trans-anethole, 37% para-cymene, 5% linalool, 2% alpha-pinene, and 39% thymol.

In some embodiments, the composition includes the following compounds in the following relative amounts, where the relative amounts of the compounds are expressed as % wt/wt: 15-25% trans-anethole, 1-10% para-cymene, 35-45% linalool, 1-10% alpha-pinene, and 30-40% thymol. In some embodiments, the composition includes the following compounds in the following relative amounts, where the relative amounts of the compounds are expressed as % wt/wt: 18.2% trans-anethole, 1.9% para-cymene, 40.8% linalool, 4.7% alpha-pinene, and 34.4% thymol.

In some embodiments, the composition includes the following compounds in the following relative amounts, where the relative amounts of the compounds are expressed as % vol/vol: 15-25% trans-anethole, 1-10% para-cymene, 35-45% linalool, 1-10% alpha-pinene, and 30-40% thymol. In some embodiments, the composition includes the following compounds in the following relative amounts, where the relative amounts of the compounds are expressed as % vol/vol: 17% trans-anethole, 2% para-cymene, 39% linalool, 5% alpha-pinene, and 37% thymol.

In some embodiments, the composition includes the following compounds in the following relative amounts, where the relative amounts of the compounds are expressed as % wt/wt: 25-35% para-cymene, 1-10% linalool, 1-10% alpha-pinene, 20-30% soy bean oil, and 35-45% thymol. In some embodiments, the composition includes the following compounds in the following relative amounts, where the relative amounts of the compounds are expressed as wt/wt: 28.39% para-cymene, 6.6% linalool, 3.8% alpha-pinene, 24% soy bean oil, and 37.2% thymol.

In some embodiments, the composition includes the following compounds in the following relative amounts, where the relative amounts of the compounds are expressed as % vol/vol: 25-35% para-cymene, 1-10% linalool, 1-10% alpha-pinene, 20-30% soy bean oil, and 35-45% thymol. In some embodiments, the composition includes the following compounds in the following relative amounts, where the relative amounts of the compounds are expressed as vol/vol: 30% para-cymene, 7% linalool, 4% alpha-pinene, 24% soy bean oil, and 35% thymol.

Surprisingly, by blending certain compounds in certain relative amounts, the resulting composition demonstrates an anti-parasitic effect that exceeds the anti-parasitic effect of any component of the composition. As used herein, "component of a composition" refers to a compound, or a subset of compounds included in a composition, e.g., the complete composition minus at least one compound. As used herein, an "anti-parasitic effect" refers to any measurable parameter related to the efficacy of a composition for treating a parasitic infection. The effect can be a parameter related to viability, killing, prophylaxis, or another useful and quantifiable parameter for a set time point, or it can be time to achieve a defined result, e.g., time to achieve 100% killing with a set dose. In this regard, when a first effect and a second effect are compared, the first effect can indicate a greater efficacy for treating a parasitic infection if it exceeds the second effect. For example, when the effect being measured is a time to achieve 100% killing, a shorter time is an anti-parasitic effect that exceeds a longer time. For another example, when the effect being measured is a % killing of target parasites, a greater % killing is an anti-parasitic effect that exceeds a lesser % killing. Effects that can be measured include, but are not limited to: time to kill a given percentage of a target parasite in vivo or in vitro; percent viability or percent killing of a target parasite in vivo or in vitro; percent viability of eggs of a target parasite; percent of a host population that is cured of an infestation by a target parasite; percent of a host population that is protected against infection by a target parasite (prophylactic effect); perturbation of a cell message or cell signal in a target parasite, such as, e.g., calcium, cyclic-AMP, and the like; and diminution of activity or downstream effects of a molecular target in a target parasite.

An exemplary in vivo method for assessing the anti-parasitic effect of a particular composition, or component of the composition, can be conducted using host animals. The host animals are infected with a target parasite. The composition or component of interest is administered to the host animal. Administration of the composition or component of interest can be initiated at various times before and/or after infection of the host animal, depending on the target parasite being tested. The eggs generated by the parasite in the host animal are quantified. For example, the eggs in a stool sample collected from the animal can be quantified. The quantification of eggs generated by the parasite in the host animal receiving the composition or component of interest can be compared the quantification of eggs generated by the parasite in another host animal, such as a host animal receiving another composition or component of interest, or a host animal serving as a control, e.g., uninfected control, or untreated control.

An exemplary in vitro method for assessing the anti-parasitic effect of a particular composition or component can be conducted using target parasites provided in test plates. The composition or component of interest is contacted with the target parasites, and the effect is observed, e.g., the effect of the composition or component of interest on the vitality of the target parasites. The effect of the treatment on the target parasites can be compared to the effect of another treatment on target parasites, such as target parasites treated with another composition or component of interest, or target parasites serving as a control, e.g., uninfected control, or untreated control.

Others methods can be used to assess the anti-parasitic effect of a particular composition or component, which methods will be evident to one of ordinary skill in the art, or can be can be determined for use in a particular case by one of ordinary skill in the art using only routine experimentation. Additional information related to assessing anti-parasitic effect can be found in the Examples set forth in this document.

In some embodiments, a synergistic anti-parasitic effect is achieved when certain compounds are blended, and the synergistic effect can be enhanced when certain compounds are blended in certain relative amounts or ratios. In other words, the compositions including certain combinations of the compounds can have an enhanced ability to treat parasitic infections, as compared to each of the compounds taken alone.

As used herein, "synergy" and "synergistic effect" can refer to any substantial enhancement, in a composition of at least two compounds, of a measurable effect, e.g., an anti-parasitic effect, when compared with the effect of a component of the composition, e.g., one active compound alone, or the complete blend of compounds minus at least one compound. Synergy is a specific feature of a blend of compounds, and is above any background level of enhancement that would be due solely to, e.g., additive effects of any random combination of ingredients.

In some embodiments, a substantial enhancement of a measurable effect can be expressed as a coefficient of synergy. A coefficient of synergy is an expression of a comparison between measured effects of a composition and measured effects of a comparison composition. The comparison composition can be a component of the composition. In some embodiments, the synergy coefficient can be adjusted for differences in concentration of the complete blend and the comparison composition.

Synergy coefficients can be calculated as follows. An activity ratio (R) can be calculated by dividing the % effect of the composition ($A_B$) by the % effect of the comparison composition ($X_n$), as follows:

$$R = A_B/X_n.\qquad\text{Formula 1}$$

A concentration adjustment factor (F) can be calculated based on the concentration ($C_n$), i.e., % (wt/wt) or % (vol/vol), of the comparison composition in the composition, as follows:

$$F = 100/C_n\qquad\text{Formula 2}$$

The synergy coefficient (S) can then be calculated by multiplying the activity ratio (R) and the concentration adjustment factor (F), as follows:

$$S = (R)(F)\qquad\text{Formula 3}$$

As such, the synergy coefficient (S) can also by calculated, as follows:

$$S = [(A_B/X_n)(100)]/C_n\qquad\text{Formula 4}$$

In Formula 4, $A_B$ is expressed as % effect of the blend, $X_n$ is expressed as % effect of the comparison composition ($X_n$), and $C_n$ is expressed as % (wt/wt) or % (vol/vol) concentration of the comparison composition in the blend.

In some embodiments, a coefficient of synergy of about 1.1, 1.2, 1.3, 1.4, or 1.5 can be substantial and commercially desirable. In other embodiments, the coefficient of synergy can be from about 1.6 to about 5, including but not limited to about 1.8, 2.0, 2.5, 3.0, 3.5, 4.0, and 4.5. In other embodiments, the coefficient of synergy can be from about 5 to 50, including but not limited to about 10, 15, 20, 25, 30, 35, 40, and 45. In other embodiments, the coefficient of synergy can be from about 50 to about 500, or more, including but not limited to about 50, 75, 100, 125, 150, 200, 250, 300, 350, 400, and 450. Any coefficient of synergy above 500 is also contemplated within embodiments of the compositions.

Given that a broad range of synergies can be found in various embodiments describe herein, it is expressly noted that a coefficient of synergy can be described as being "greater than" a given number and therefore not necessarily limited to being within the bounds of a range having a lower and an upper numerical limit. Likewise, in some embodiments described herein, certain low synergy coefficients, or lower ends of ranges, are expressly excluded. Accordingly, in some embodiments, synergy can be expressed as being "greater than" a given number that constitutes a lower limit of synergy for such an embodiment. For example, in some embodiments, the synergy coefficient is equal to or greater than 25; in such an embodiment, all synergy coefficients below 25, even though substantial, are expressly excluded.

In some embodiments, synergy or synergistic effect associated with a composition can be determined using calculations similar to those described in Colby, S. R., "Calculating synergistic and antagonistic responses of herbicide combinations," *Weeds* (1967) 15:1, pp. 20-22, which is incorporated herein by this reference. In this regard, the following formula can be used to express an expected % effect (E) of a composition including two compounds, Compound X and Compound Y:

$$E = X + Y - (X*Y/100)\qquad\text{Formula 5}$$

In Formula 5, X is the measured actual % effect of Compound X in the composition, and Y is the measured actual % effect of Compound Y of the composition. The expected % effect (E) of the composition is then compared to a measured actual % effect (A) of the composition. If the actual % effect (A) that is measured differs from the expected % effect (E) as calculated by the formula, then the difference is due to an interaction of the compounds. Thus, the composition has synergy (a positive interaction of the compounds) when A>E. Further, there is a negative interaction (antagonism) when A<E.

Formula 5 can be extended to account for any number of compounds in a composition; however it becomes more complex as it is expanded, as is illustrated by the following formula for a composition including three compounds, Compound X, Compound Y, and Compound Z:

$$E = X + Y + Z - ((XY + XZ + YZ)/100) + (X*Y*Z/10000)\qquad\text{Formula 6}$$

An easy-to-use formula that accommodates compositions with any number of compounds can be provided by modifying Formulas 5 and 6. Such a modification of the formula will now be described. When using Formulas 5 and 6, an untreated control value (untreated with composition or compound) is set at 100%, e.g., if the effect being measured is the amount of target parasites killed, the control value would be set at 100% survival of target parasite. In this regard, if treatment with Compound A results in 80% killing of a target parasite, then the treatment with Compound A can be said to result in a 20% survival, or 20% of the control value. The relationship between values expressed as a percent effect and values expressed as a percent-of-control are set forth in the following formulas, where E' is the expected % of control of the composition, $X_n$ is the measured actual % effect of an individual compound (Compound $X_n$) of the composition, $X_n'$ is the % of control of an individual compound of the composition, and A' is the actual measured % of control of the of the composition.

$$E = 100 - E' \quad \text{Formula 7}$$

$$X_n = 100 - X_n' \quad \text{Formula 8}$$

$$A = 100 - A' \quad \text{Formula 9}$$

By substituting the percent-of-control values for the percent effect values of Formulas 5 and 6, and making modifications to accommodate any number (n) of compounds, the following formula is provided for calculating the expected % of control (E') of the composition:

$$E' = \left(\sum_{i=1}^{n} X_i'\right) \div 100^{n-1} \quad \text{Formula 10}$$

According to Formula 10, the expected % of control (E') for the composition is calculated by dividing the product of the measured actual % of control values ($X_n'$) for each compound of the composition by $100^{n-1}$. The expected % of control (E') of the composition is then compared to the measured actual % of control (A') of the composition. If the actual % of control (A') that is measured differs from the expected % of control (E') as calculated by the Formula 10, then the difference is due to an interaction of the compounds. Thus, the composition has synergy (a positive interaction of the compounds) when A'<E'. Further, there is a negative interaction (antagonism) when A'>E'.

Compositions containing two or more compounds in certain ratios or relative amounts can be tested for a synergistic effect by comparing the anti-parasitic effect of a particular composition of compounds to the anti-parasitic effect of a component the composition. Additional information related to making a synergy determination can be found in the Examples set forth in this document.

It is contemplated that the compositions of the presently-disclosed subject matter could be formulated for and delivered by carriers, including food products. For example, additives are added to baked goods, such as cookies, breads, cakes, etc., to enhance or modify flavor or color, increase shelf life, enhance their nutritional value, and generally produce a desired effect. Similarly, compositions of the presently-disclosed subject matter could be formulated with food products as carriers and delivered by ingestion to produce their desired effect. Of course, numerous types of foods could be used to deliver the compositions, including but not limited to: beverages, breakfast cereals, and powdered drink mixes.

Further, the compositions disclosed herein can take such forms as suspensions, solutions or emulsions in oily or aqueous carriers, and can contain formulatory agents such as suspending, stabilizing and/or dispersing agents. For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art. For example, a composition disclosed herein can be formulated having an enteric or delayed release coating which protects the composition until it reaches the colon.

Liquid preparations for oral administration can take the form of, for example, solutions, syrups or suspensions. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). Liquid preparations for oral administration can also be formulated for delayed release, such as for example in "gel caps".

In certain embodiments, the compositions could be provided in an encapsulated or microencapsulated form. Microencapsulation is a process where small particles of the composition are coated or encapsulated with an outer shell material for controlling the release of the composition or for protecting the composition. Exemplary outer shell material includes proteins, polysaccharides, starches, waxes, fats, natural and synthetic polymers, and resins. Microencapsulation can be done either chemically or physically. For example, physical methods of encapsulating the compositions could include: spray drying, spray chilling, pan coating, or coextrusion. Chemical methods of encapsulation could include coacervation, phase separation, solvent extraction, or solvent evaporation.

As one example, for coextrusion of a liquid core, liquid core and shell materials are pumped through concentric orifices, with the core material flowing in the central orifice, and the shell material flowing through the outer annulus. An enclosed compound drop is formed when a droplet of core fluid is encased by a layer of shell fluid. The shell is then hardened by appropriate means; for example, by chemical cross-linking in the case of polymers, cooling in the case of fats or waxes, or solvent evaporation. Additional information about methods and systems for providing compositions formulated for and delivered via food products can be found in U.S. Pat. Nos. 5,418,010, 5,407,609, 4,211,668, 3,971,852, and 3,943,063, each of which is incorporated herein by this reference.

The compositions of the presently-disclosed subject matter can be used for treating parasitic infections. The presently-disclosed subject matter includes methods for treating a parasitic infection in a subject, including administering an effective amount of a composition described herein.

As used herein, the terms "host" and "subject" are used interchangeably and refer to a plant or an animal capable of being infected by a parasite. The animal can be a vertebrate. The vertebrate can be warm-blooded. The warm-blooded vertebrate can be a mammal. The mammal can be a human. The human can be an adult or a child. As used herein, the terms "host" and "subject" include human and animal hosts and subjects. Thus, veterinary therapeutic uses are provided in accordance with the presently-disclosed subject matter. As such, the presently-disclosed subject matter provides for the treatment of mammals such as humans, as well as those mammals of importance due to being endangered, such as Siberian tigers or snow leopards; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

As used herein, the terms "treat," "treating," and "treatment" refer to: conferring protection against infection; preventing infection; alleviating infection; reducing the severity of symptoms and/or sequelae of infection; eliminating infection; and/or preventing relapse of infection. As used herein, the terms "treat," "treating," and "treatment" also refer to conferring protection against, preventing, alleviating, reducing the severity of, eliminating, and/or preventing relapse associated with a disease or symptoms caused by a parasitic infection.

As used herein, the term "effective amount" refers to a dosage sufficient to provide treatment for a parasitic infection. The exact amount that is required can vary, for example, depending on the target parasite, the treatment being affected, age and general condition of the subject, the particular formulation being used, the mode of administration, and the like. As such, the effective amount will vary based on the particular circumstances, and an appropriate effective amount can be determined in a particular case by one of ordinary skill in the art using only routine experimentation.

The presently-disclosed subject matter includes methods of screening for compositions useful for treating a parasitic infection. In some embodiments, the screening method is useful for narrowing the scope of possible compounds that are identified for as components for a composition for treating a parasitic infection.

In some embodiments, a method of selecting a composition for use in treating a parasitic infection includes the following. A cell expressing a tyramine receptor is provided and is contacted with test compounds. The receptor binding affinity of the compounds is measured. At least one parameter selected from the following parameters is measured: intracellular cAMP level, and intracellular $Ca^{2+}$ level. A first compound for the composition is identified, which is capable of altering at least one of the parameters, and which has a high receptor binding affinity for the tyramine receptor; and a second compound for the composition is identified, which is capable of altering at least one of the parameters, and which has a low receptor binding affinity for the tyramine receptor. A composition is selected that includes the first and second compounds. In some embodiments, a composition is selected that includes the first and second compounds and demonstrates an anti-parasitic effect that exceeds the anti-parasitic effect of any of the compounds when used alone.

The cell used for the method can be any cell capable of being transfected with and express a Tyramine Receptor (TyrR). Examples of cells include, but are not limited to: insect cells, such as *Drosophila* Schneider cells, *Drosophila* Schneider 2 cells (S2 cells), and *Spodoptera frugiperda* cells (e.g., Sf9 or Sf21); or mammalian cells, such as Human Embryonic Kidney cells (HEK-293 cells), African green monkey kidney fibroblast cells (COS-7 cells), HeLa Cells, and Human Keratinocyte cells (HaCaT cells). Additional information about preparing cells expressing receptors can be found in U.S. patent application Ser. Nos. 10/832,022; 11/086,615; and 11/365,426, which are incorporated herein in their entirety by this reference.

The tyramine receptor (TyrR) can be a full-length TyrR, a functional fragment of a TyrR, or a functional variant of a TyrR. A functional fragment of a TyrR is a TyrR in which amino acid residues are deleted as compared to the reference polypeptide, i.e., full-length TyrR, but where the remaining amino acid sequence retains the binding affinity of the reference polypeptide for tyramine. A functional variant of a TyrR is a TyrR with amino acid insertions, amino acid deletions, or conservative amino acid substitutions, which retains the binding affinity of the reference polypeptide for tyramine. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another. A conservative amino acid substitution also includes replacing a residue with a chemically derivatized residue, provided that the resulting retains the binding affinity of the reference polypeptide for tyramine. Examples of TyrRs include, but are not limited to: TyrRs, such as, *Drosophila melanogaster* TyrR (GENBANK® accession number (GAN) CAA38565), *Locusta migratoria* TyrR (GAN: Q25321), TyrRs of other invertebrates, and TyrRs of nematodes, including *Ascaris*.

In some embodiments, other receptors, such as G-protein coupled receptors (GPCRs), whether having native affinity for tyramine or other ligands, can be employed in methods of screening for compositions useful for treating a parasitic infection. Examples of receptors that can be used include, but are not limited to: *Anopheles gambiae* (GAN: EAA07468), *Heliothis virescens* (GAN: Q25188), *Mamestra brassicae* (GAN: AAK14402), *Tribolium castaneum* (GAN: XP_970290), *Aedes aegypti* (GAN: EAT41524), *Boophilus microplus* (GAN: CAA09335); *Schistosoma mansoni* (GAN: AAF73286); and *Schistosoma mansoni* (GAN: AAW21822).

Some of the receptors disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein.

As used herein, the term "receptor binding affinity" refers to an interaction between a composition or component, e.g., compound, and a receptor binding site. The interaction between a composition or component, and the receptor binding site, can be identified as specific or non-specific. In some embodiments, the specificity of an interaction between a composition or component, and a TyrR binding site, can be determined in the following manner. A wild type fly (*Drosophila melanogaster*) and a mutant fly are provided, where the mutant fly lacks a TyrR. The wild type and mutant flies are exposed to a composition or component of interest. If the exposure negatively affects the wild type fly, (e.g., knock down, death), but does not negatively affect the mutant fly, then the treatment with the composition or component of interest can be said to be specific for the TyrR. If the exposure negatively affects the wild type fly and the mutant fly, then the treatment with the composition or component of interest can be said to be non-specific for the TyrR.

A "high receptor binding affinity" can be a specific interaction between a composition or component, and the receptor binding site. In some embodiments, a high receptor binding affinity is found when the equilibrium dissociation constant ($K_d$) is less than about 100 nM, 75 nM, 50 nM, 25 nM, 20 nM, 10 nM, 5 nM, or 2 nM. In some embodiments, a high receptor binding affinity is found when the equilibrium inhibitor dissociation constant ($K_i$) is less than about is less than about 100 μM, 75 μM, 50 μM, 25 μM, 20 μM, 10 μM, 5 μM, or 2 μM, when competing with tyramine. In some embodiments, a high receptor binding affinity is found when the effective concentration at which tyramine binding is inhibited by 50% ($EC_{50}$) is less than about 500 μM, 400 μM, 300 μM, 100 μM, 25 μM, or 10 μM.

A "low receptor binding affinity" can be a non-specific interaction between a composition or component, and the receptor binding site. In some embodiments, a low receptor binding affinity is found when the equilibrium dissociation constant ($K_d$) is greater than about 100 nM, 125 nM, 150 nM, 175 nM, 200 nM, 225 nM, or 250 nM. In some embodiments, a low receptor binding affinity is found when the equilibrium inhibitor dissociation constant ($K_i$) is greater than about 100 μM, 125 μM, 150 μM, 175 μM, 200 μM, 225 μM, or 250 μM, when competing with tyramine. In some embodiments, a low receptor binding affinity is found when the effective concentration at which tyramine binding is inhibited by 50% ($EC_{50}$) is greater than about 500 μM, 625 μM, 750 μM, 875 μM, 1000 μM, 1125 μM, or 1250 μM.

Unless defined otherwise, all technical and scientific terms used herein have the same meaning as commonly understood by one of ordinary skill in the art to which the presently-disclosed subject matter belongs. Although any methods and materials similar or equivalent to those described herein can be used in the practice or testing of the presently-disclosed subject matter, representative methods and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter. As used herein, the term "about," when referring to a value or to an amount of mass, weight, time, volume, concentration, or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The presently-disclosed subject matter is further illustrated by the following specific but non-limiting examples. The following examples may include compilations of data that are representative of data gathered at various times during the course of development and experimentation related to the presently-disclosed subject matter. The following examples include prophetic examples.

EXAMPLES

Examples 1-3

An example of a parasite that commonly infects humans is *Hymenolepsis nana*, which is an intestinal parasite. *H. nana* is a difficult worm to eliminate from the human intestine. See John Rim, Treatment of *Hymenolepis nana* infection. *Post-Graduate Doctor Journal*. Middle East Edition, 5:330-334, 1985. *H. nana* is found worldwide and infection can occur in humans of any age; however, due to the increased likelihood of exposure to human feces, small children have the highest risk of contracting hymenolepiasis, the disease associated with *H. nana* infection.

*H. nana* has a characteristic life cycle of about 7 days. When a host has been infected, the *H. nana* eggs pass into the ileum of the small intestine and hatch into oncospheres, motile larvae of *H. nana*, which penetrate the lamina propria of the villus of the small intestine. Within about 3 to 4 days, the larvae mature into pre-adult cysticercoids, which then enter the gut lumen, attaching to the mucosa of the villus of the small intestine. Many infections are asymptomatic, keeping some infected individuals from seeking medical treatment and being cured. Symptomatic forms of the infection are characterized by irritability, diarrhea, abdominal pain, restless sleep, anal pruritus, nasal pruritus, behavior disturbance, and seizures.

In the present Examples, *Hymenolepis nana* is selected as an exemplary parasite used to study the efficacy in vitro and in vivo of compositions disclosed herein for treating parasitic infections. Laboratory-raised Swiss albino mice are used as host animals. Uninfected males and females are used. Pregnant females are isolated from other mice. The newly born litters are maintained to avoid infection thereof. The mother mice are checked twice weekly by direct saline fecal smear and the negative sample is re-examined by zinc sulphate centrifugation floatation and saline sedimentation techniques to exclude those parasitologically infected. See Melvin and Brooke, Laboratory procedures for the diagnosis of intestinal parasites. DHEW Publications No. (CDC) 76-828, Public Health Services, 1975, incorporated herein by reference in its entirety.

After weaning the litters, the mice are checked twice weekly and uninfected litters are used for the Examples. Mice are kept under scrupulous hygienic conditions and fed one day milk and the other day wheat. Diet and water are available ad libitum.

Eggs of *H. nana*, free of debris, teased from gravid segments are used for infection. See Ito, In vitro oncospheral agglutination given by immune sera from mice infected and rabbits injected with eggs of *Hymenolepis nana*. Parasito, 71: 465, 1975, incorporated herein by reference in its entirety. Prior to inoculation, the egg shells are removed and every mouse is inoculated with a known number of eggs to maintain the infection cycle. See Bernetzen and Voge, In vitro hatching of oncosphere of Hymenolepidid cestodes. *J. Parasitol.*, 5:235, 1965, incorporated herein by reference in its entirety.

Maximum tolerated dose (MTD) of each test agent is determined before starting the in vivo study. Worm-free 5 weeks old mice (25-30 grams) are used in the experiment. Each mouse is inoculated with 150 eggs. Then they are subdivided into groups, each group containing 15 mice. Each of these groups is specified for testing the efficacy of one test agent as a potential therapeutic drug against adult worm of *Hymenolepis nana*. A control group composed of 15 mice is also infected with the same number of eggs but not subjected to the test agents. Infection is monitored and a base egg count from feces is determined for each mouse (experimental and control groups).

Example 1

The following compositions were each tested for anti-parasitic effects against *H. nana* in vivo: Rx1—Black seed cumin oil; Rx2—Lilac flower oil; Rx3—thyme oil (white); Rx4—carvacrol; Rx5—geraniol; Rx6—cineol; and Rx7—wintergreen oil; Rx8—Lilac Flower oil-V3; Rx9—trans-anethole; Rx10—p-cymene; Rx11—thymol.

Each mouse in the experimental groups was inoculated orally with 400 mg/kg body weight of the specified test compound (Rx) daily for 5 successive days beginning 24 hours following detection of eggs in feces. At the same time, each mouse of the control group was inoculated orally with 400 mg/kg body weight of the suspension material only, i.e. soybean oil, daily for 5 successive days. The egg count of every mouse (experimental and control) was determined daily during the periods of treatment and for further 2 days after the last dose treatment. On the 3rd day after the last dose treatment the cure rate was determined. The criteria for cure was assessed according to: (1) determination of egg-reduction rate; and (2) the absence of the adult worms. The mouse being assessed was killed by decapitation and the small intestine dissected for detecting the adult worms.

With reference to Table 1 and FIG. 1 the cure rate ranged between about 30% to about 70% following treatment with the tested compounds. An infected animal was determined to be cured when it was completely free of worms and eggs at the time of assessment. Various compositions showed a significant cure rate, including: Rx2 (cure rate: 71.4%), Rx5 (cure rate: 66.6%), and Rx7 (cure rate: 60%).

TABLE 1

| Variable | Egg Count (X ± SD) | | | | | | | |
| --- | --- | --- | --- | --- | --- | --- | --- | --- |
|  | Control | Rx 1 | Rx 2 | Rx 3 | Rx 4 | Rx 5 | Rx 6 | Rx 7 |
| Pre Treatment (Base Line Data) | 3 ± 1 | 2 ± 1 | 3 ± 1.2 | 3 ± 1.2 | 3 ± 1 | 3 ± 1 | 3.1 ± 1.2 | 3 ± 1 |
| During Treatment |  |  |  |  |  |  |  |  |
| 1st Day | 3 ± 1 | 2 ± 1 | 1 ± 1.2 | 12 ± 9.1 | 5 ± 0.6 | 14 ± 13.9 | 5 ± 9.5 | 1.4 ± 1.1 |
| 2nd Day | 5 ± 9.5 | 17.7 ± 45.9 | 0.8 ± 0.9 | 26 ± 25.6 | 2.2 ± 3.4 | 1.4 ± 2.1 | 3.8 ± 14.3 | 10.6 ± 17.9 |
| 3rd Day | 31 ± 14 | 17.5 ± 19 | 1.8 ± 2.5 | 66 ± 57.9 | 1 ± 1.9 | 4.1 ± 9.6 | 1 ± 1.2 | 22.7 ± 39.7 |
| 4th Day | 27 ± 17 | 33.4 ± 55.7 | 3.3 ± 3.2 | 25.4 ± 15.4 | 0.9 ± 1.2 | 2.6 ± 7.4 | 1.8 ± 1.7 | 9.8 ± 13.2 |
| 5th Day | 5.3 ± 4.7 | 33.5 ± 25.7 | 1.7 ± 1.8 | 5.3 ± 8.9 | 2 ± 2 | 2.3 ± 3.6 | 1.6 ± 1.5 | 1.6 ± 1.7 |
| Post treatment |  |  |  |  |  |  |  |  |
| 2 Days after last dose | 125 ± 42.1 | 75.8 ± 21.3 | 2 ± 3.6 | 17.5 ± 20.3 | 1.3 ± 1.1 | 0.5 ± 0.9 | 2.5 ± 3.5 | 2.8 ± 5.2 |
| 3 Days after last dose |  |  |  |  |  |  |  |  |
| Positiveity rate (%) | 100 | 66.7 | 28.6 | 66.7 | 71.4 | 33.4 | 45.5 | 40 |
| Cure rate (%) | 0 | 33.3 | 71.4 | 33.3 | 28.6 | 66.6 | 54.5 | 60 |

Post treatment dissection of the positive infected mice showed the following: the worms were intact, living, and active; the scolex (head) of the worm was intact keeping its anatomical feature with moving rostellum and contracting suckers; the neck, which is considered the area of segmentation (producing new segments), was intact; and the strobila (the body of the worm) was intact, maintaining its anatomical feature with 3 groups of segments (immature segments or segments with immature reproductive organs, mature segments or segments with mature reproductive organs, and gravid segments or segments with uteri full of mature eggs). Worms were absent or dead in mice treated for 5 consecutive days with Rx2 (71%), Rx5 (67%), and Rx7 (60%).

These experiments can also be conducted to study the treatment efficacy of the presently-disclosed compositions against *Trichuris trichiura* in vivo.

Example 2

The compounds are combined to produce the compositions having anti-parasitic properties disclosed herein. The compositions tested are set forth in Table 2. An "X" in a cell of the table indicates that a particular compound is included in a particular test composition. For example, in the column labeled "S1," there is an X in the row setting forth thymol. As such, composition "S1" includes Thymol. Composition S1 further includes carvacrol, trans-anethole, and p-cymene.

TABLE 2

| | S1 | S2 | S3 | S4 | S5 | S6 | S7 | S8 | S9 | S10 | S11 | S12 | S13 | S14 | S15 | S16 |
|---|---|---|---|---|---|---|---|---|---|---|---|---|---|---|---|---|
| thymol | X | | X | X | | | | X | | | | X | X | | X | X |
| thyme oil (white) | | X | | X | | X | | X | | X | X | | | X | | |
| linalool | | | | | | | | | | | | | | | | X |
| carvacrol | X | X | X | X | X | | | | | | | | | | | |
| trans-anethole | X | X | X | X | | | X | | | | | | | | | |
| α-pinene | | | | | | | | | | | | | | | | X |
| p-cymene | X | X | | | | | | | | | | | | | | X |
| black seed cumin oil | | | | | | | | X | | X | | X | | | | |
| Lilac flower oil | | | | | | | | | X | | X | | X | | | |
| geraniol | | | | | | | | X | X | | | X | X | | | |
| wintergreen oil | | | | | | | | | | | | | | X | X | |
| cineol | | | | | | | | | | | | | | X | X | |
| lime oil | | | | | | | | X | | X | X | | | | | |
| d-limonene | | | | | | | | | X | | | | | | | |

Each mouse in the experimental groups is inoculated orally with 400 mg/kg body weight of the specified test composition daily for 5 successive days. At the same time, each mouse of the control group is inoculated orally with 400 mg/kg body weight daily for 5 successive days of the suspension material only, i.e. soybean oil. The egg count of every mouse (experimental and control) is determined daily during the periods of treatment and for a further 2 days after the last dose treatment. On the 3rd day after the last dose treatment the cure rate is determined. The criteria for cure are assessed according to: (1) determination of egg-reduction rate; and (2) the absence of adult worms. The mouse being assessed is killed by decapitation and the small intestine is dissected for detecting the adult worms.

The cure rate is expected to be between about 25% and 80% following treatment with compositions S1 through S16. An infected animal is determined to be cured when it is completely free of worms and eggs at the time of assessment. Worms are absent or dead in mice treated for multiple consecutive days with the compositions having cure rates of about 60% or higher.

These experiments can also be conducted to study the treatment efficacy of the presently-disclosed compositions against *Trichuris trichiura* in vivo.

Example 3

The following compounds and blend compositions were each tested for anti-parasitic effects against *H. nana* in vivo: (1) p-cymene; (2) thymol; (3) α-pinene; (4) linalool; (5) soybean oil (control); and (6) blend of 30% p-cymene, 35% thymol, 4% α-pinene, 7% linalool, and 24% soybean oil, where percentages are by weight.

Each mouse in the groups was inoculated orally with 100 mg/kg body weight of the specified compound or blend composition daily for 5 successive days. The egg count of each mouse (experimental and control) was determined daily during the periods of treatment and for 2 more days after the last dose treatment. Following the 3rd day of the last dose treatment the cure rate was determined. The criteria for cure was assessed according to: (1) determination of egg-reduction rate; and (2) the absence of the adult worms. The mouse being assessed was killed by decapitation and the small intestine dissected for detecting the adult worms.

With reference to Table 3, the cure rate ranged from 0%, for the soybean oil (control), to 100%, for the blend composition containing 30% p-cymene, 35% thymol, 4% α-pinene, 7% linalool, and 24% soybean oil. Cure rate represents the number of infected animals that demonstrate no eggs in their stool and no worms found in their intestine following treatment with the tested compounds.

TABLE 3

| Group | Compound | Tested dose (mg/kg b.w.) | Cure rate (%) |
|---|---|---|---|
| 1 | p-cymene | 100 | 13.3 |
| 2 | thymol | 100 | 33.3 |
| 3 | α-pinene | 100 | 25.0 |
| 4 | linalool | 100 | 23.3 |
| 5 | soybean oil (control) | 100 | 00.0 |
| 6 | blend composition* | 100 | 100 |

*30% p-cymene, 35% thymol, 4% α-pinene, 7% linalool, and 24% soybean oil

As indicated by the data above, the blend composition has a synergistic effect, as compared to the individual compounds that are components of the blend. A coefficient of synergy can be calculated for the blend, relative to each individual compound, i.e., comparison composition. Such synergy coefficients are set forth in Table 4.

TABLE 4

| Comparison Composition | Cure rate (%) | Activity Ratio | Concentration of Comparison Composition in Blend (%, by wt) | Concentration Adjustment Factor | Synergy Coefficient |
|---|---|---|---|---|---|
| p-cymene | 13.3 | (1.00)/(0.133) = 7.52 | 30 | (1.00)/(0.300) = 3.33 | 25.1 |
| thymol | 33.3 | (1.00)/(0.333) = 3.00 | 35 | (1.00)/(0.350) = 2.86 | 8.57 |
| α-pinene | 25.0 | (1.00)/(0.250) = 4.00 | 4 | (1.00)/(0.040) = 25.0 | 100 |
| linalool | 23.3 | (1.00)/(0.233) = 4.29 | 7 | (1.00)/(0.070) = 14.29 | 61.3 |

TABLE 4-continued

| Comparison Composition | Cure rate (%) | Activity Ratio | Concentration of Comparison Composition in Blend (%, by wt) | Concentration Adjustment Factor | Synergy Coefficient |
|---|---|---|---|---|---|
| soybean oil (control) | 00.0 | — | 24 | (1.00)/(0.240) = 4.17 | — |
| blend | 100 | (1.00)/(1.00) = 1.00 | 100 | (1.00)/(1.00) = 1.00 | 1.00 |

For example, the activity ratio for p-cymene is 7.52 because the effect of the blend is a cure rate of 100%, while the effect of p-cymene alone is 13.3% [(1.00)/(0.133)=7.52]. The concentration adjustment factor for p-cymene is 3.33 because the blend contains 30% p-cymene, as compared to the 100% p-cymene tested alone [(1.00)/(0.300)=3.33]. The synergy coefficient of the blend, relative to p-cymene ($S_{p\text{-}cymene}$) is therefore 25.1 [((1.00)/(0.133))/(0.300)=25.1]. With further reference to Table 4, the synergy coefficients for the blend are as follows: $S_{p\text{-}cymene}$=25.1; $S_{thymol}$=8.57; $S_{\alpha\text{-}pinene}$=100; and $S_{linalool}$=61.3.

Example 4

In the present Example, *Schistosoma mansoni* is selected as an exemplary parasite used to study the efficacy in vivo of compositions disclosed herein for treating parasitic infections. Assessment of the efficacy of the tested compositions against *S. mansoni* infection is with regard to worm load, sex ratio of worms, distribution of worms, fecundity of female worms, and egg deposition in liver and intestine.

Female Swiss Albino mice, 8 weeks in age, from 18-22 gm in weight, which can be obtained from Theodore Bilharz research Institute, Cairo, are infected percutaneously by *S. mansoni* cercariae (100 cercariae/mouse), Each group consists of 15 mice.

For each test composition, three concentrations are tested. For each concentration nine groups of mice are studied. One group of *S. mansoni*-infected mice receives Praziquantel (PZQ), which is the present standard antischistosomal drug. Three groups of uninfected mice receive the test compound in the same schedule and concentration as the test drug groups. One group of uninfected and untreated mice and one group of *S. mansoni* infected mice that do not receive any treatment are maintained as controls.

Three different concentrations from each of the test compositions are determined after estimation of the $LD_{50}$. The schedule for drug administration is as follows: (1) four days post-infection (PI); (2) one week PI; and seven weeks PI. Praziquantel (Distocide), 600 mg/Kg body weight, is administered seven weeks PI. All drugs are administered orally using a stomach tube.

For the parasitological studies, fecal egg counts are done for all infected groups twice weekly starting from the $5^{th}$ week PI.

Mice are sacrificed 9 weeks PI. Perfusion of the portal system is done for the recovery of the schistosome worms. The total number, sex, maturation and distribution of the worms are determined. Four portions, two from the jejunum and two from the ileum, are taken from each mouse, washed with PBS, opened and compressed between two slides and examined microscopically for detection of the stage of maturation. 0.3 gram of the liver and of the intestine are digested in 4% potassium hydroxide overnight, and *S. mansoni* ova counted.

Example 5

Three groups of mice are treated with each test compound or composition blend of compounds. For Groups 1 and 2, treatment starts 4 and 7 days after infection, respectively. For Group 3, treatment starts 7 weeks after infection. For the control group, the mice are injected 7 weeks after infection with Praziquantel at 600 mg/kg. Efficacy of test agents is determined based on: worm load; sex ratio; distribution of worms; fecundity of female worms; and egg deposition in liver and intestine.

Example 6

Adult male and female *S. mansoni* were collected from infected mice and transferred into 100 ml saline treated with test compositions Rx1-Rx10 (as disclosed in Example 1) or Praziquantel at varying concentrations and incubated at 37° C. in 5% CO2. In many cases adult male and females are collected as couples. Viability of worms is examined under a binuclear microscope. Controls are treated in parallel. The experiment is terminated either when all worms are dead in the treated samples or when the first death among controls is found.

Figure 2:
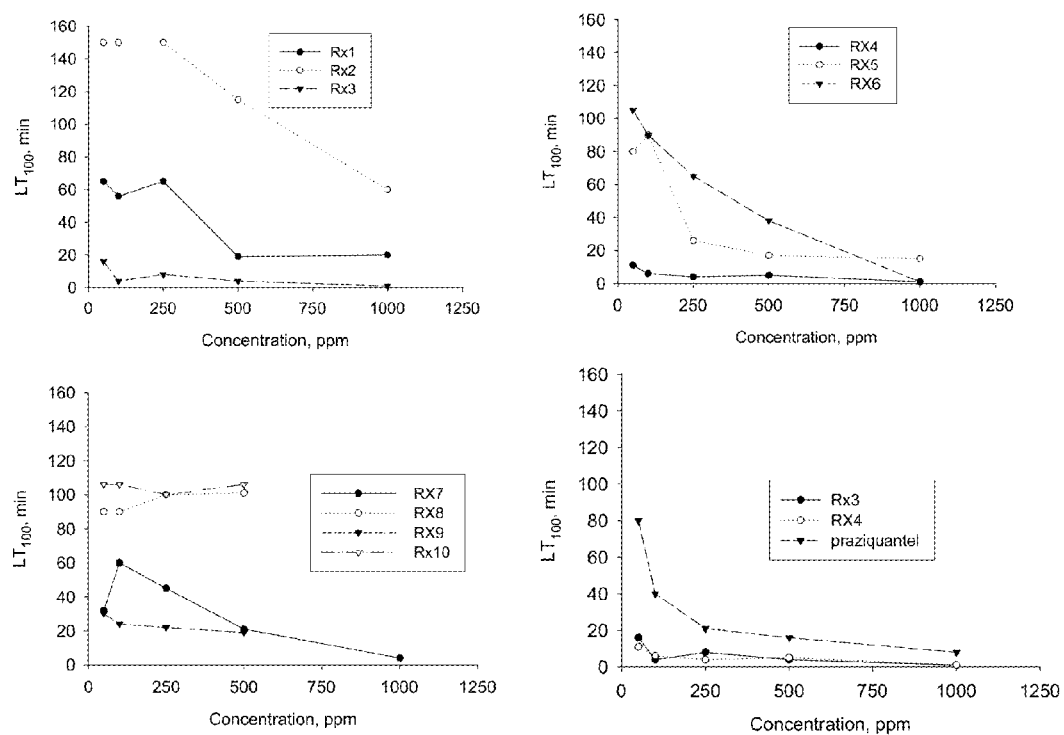
FIG. 2 is a series of line graphs demonstrating effective killing of *S. mansoni* in vitro by differing concentrations of compounds disclosed herein. LT100=lethal time required to induce 100% mortality among treated worms. ppm=mg (weight) in 1 L (volume). For example 100 ppm equal 100 mg (weight) in 1 L (volume) saline.
Figure 3:
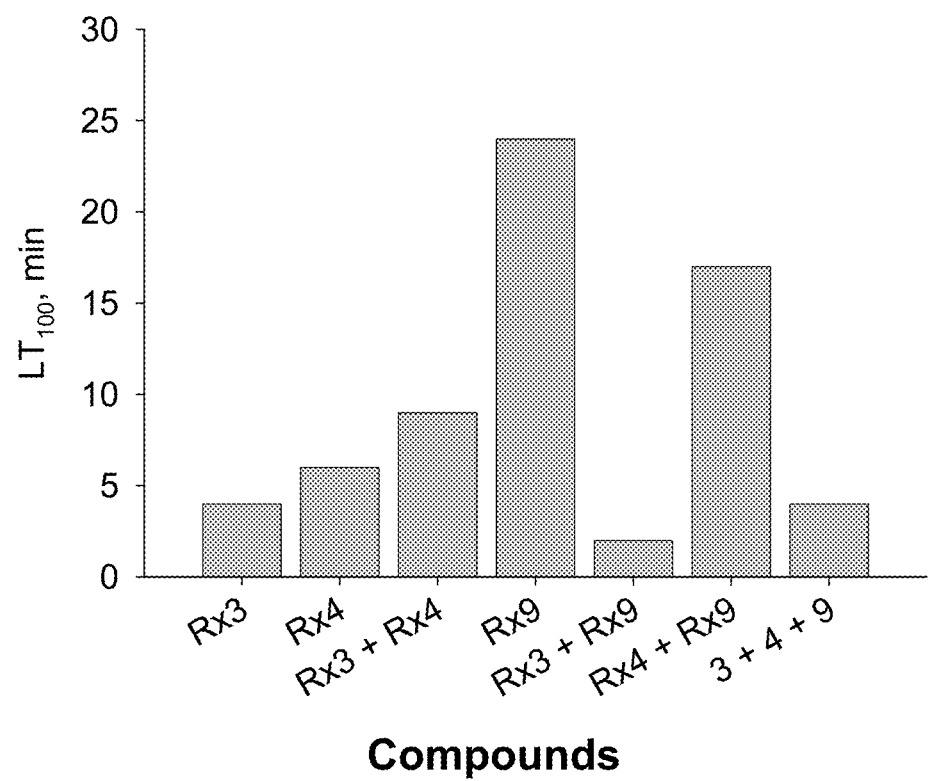
FIG. 3 is a bar graph demonstrating effective killing of *S. mansoni* in vitro by 100 ppm concentration of compounds disclosed herein, either alone or in combination with one another. LT100=lethal time required to induce 100% mortality among treated worms.

Each of the compounds were tested individually at differing concentrations and the data from these experiments are presented in FIG. 2. Next, each compound was tested by itself at 100 ppm final concentration and then compositions were combined at 1:1 ratios when two compounds were combined or 1:1:1 ratios when three compounds were combined and each combined composition tested at 100 ppm final concentration. Data from these experiments are presented in FIG. 3.

Example 7

The present Example provides an in vitro study testing treatment of *Histomonas meleagridis*, a protozoan parasite causing blackhead disease of chickens and turkeys, using the presenit-disclosed compounds and blend compositions of the compounds.

*H. meleagridis* is cultured in vitro and prepared for use in screw-capped glass vials containing 1 ml of Dwyer's medium and inoculated with 20,000 cells. The test compounds and/or compositions are diluted to appropriate concentrations, so that the desired dose is administered to the tubes in 0.1 ml. Each treatment is replicated in duplicate cultures. The cultures are incubated for 2 days.

The number of *H. meleagridis* cells/ml can be counted using a standard hemocytometer (Neubauer) and the actual number of cells/ml is reported.

Figure 4:
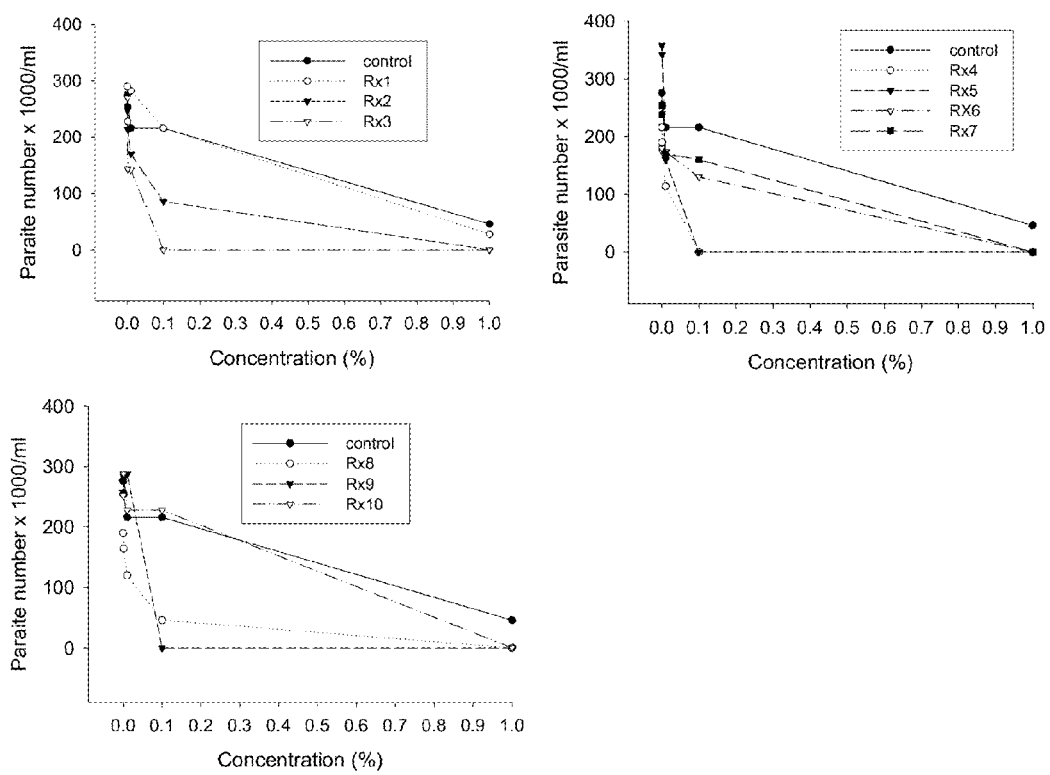
FIG. 4 is a series of line graphs demonstrating effective killing of *H. meleagridis* in vitro by differing concentrations of compounds disclosed herein.
Figure 5:
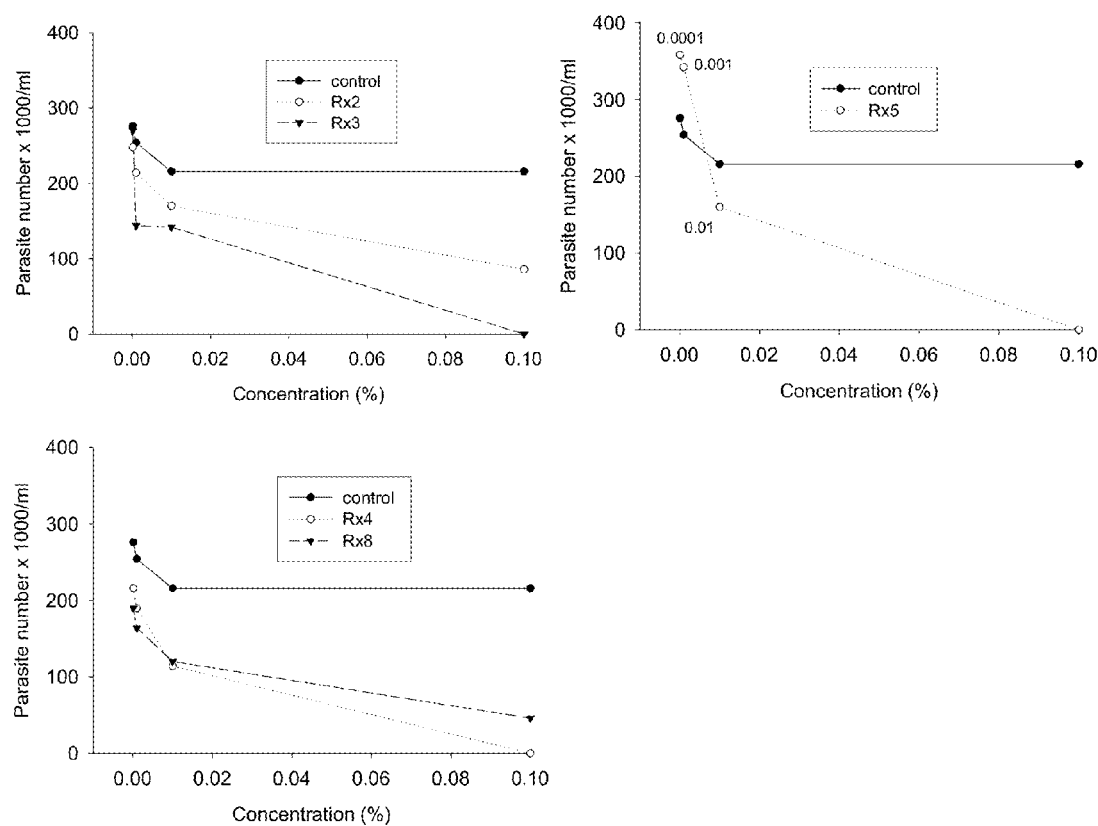
FIG. 5 is a series of line graphs demonstrating effective killing of *H. meleagridis* in vitro by differing concentrations of compounds disclosed herein.

Each compound and/or composition is tested at 1, 0.1, 0.01, 0.001 and 0.0001%. Controls are included as untreated and with solvent (ethanol). Data from the experiments are presented in FIGS. 4 and 5.

Example 8

*Trichuris trichiura* is a common nematode infection worldwide. The highest prevalence occurs in tropic climates with poor sanitation practices, as it has fecal/oral transmission.

*Trichuris trichiura* does not migrate through the tissues, and it does not cause eosinophilia. It can survive 6 yrs. in host (average 3 years), living in the large intestine with its head imbedded in intestinal mucosa, but there is virtually no cellular response. Diagnosis of *Trichuris trichiura* is made through finding the eggs in feces.

Infection with *Trichuris trichiura* is frequently asymptomatic. However, in heavy infection in undernourished children, *Trichuris trichiura* can cause rectal prolapse following chronic bloody diarrhea.

Compounds and blended compositions of the compounds, as disclosed herein, can be tested for in vitro anti-parasitic activity using the protocols following. Ten groups (8 different concentrations of compositions and 2 controls) can be tested. Tests are performed in sterile six well plates with 1-4 worms per well. Each well contains 3 mL RPMI 1640 containing a 10× antibiotic/antimycotic (penicillin/streptomycin/amphotercin B) solution to prevent overgrowth of contaminating organisms. Worm motility is observed at all initial time points, as well as 24 hour post treatment, i.e. following wash and placement in media without test compounds.

As indicated, eight concentrations and two controls are tested. The controls indicated for these tests will be a surfactant control and a media control. The protocol utilizes 5-10× of the final concentrations of test compounds to be added to the media at the time of testing.

Once the test is initiated, motility is checked at 15, 30, 60, 120, 240, and 360 minutes post-treatment. Following the last time point, the worms are removed from the treated media, rinsed and placed into untreated media. A last motility check is performed at 24 post treatment. Worms not observed to be motile are prodded with a sterile (autoclaved) wooden applicator stick to confirm lack of responsiveness.

Example 9

Compounds and blended compositions of the compounds, as disclosed herein, can be tested for in vitro anti-parasitic activity using the protocols following. Ten groups (8 different concentrations of compositions and 2 controls) can be tested. Tests are performed in sterile 150 cm$^3$ flasks with 1-2 worms per flask. Each flask contains 200 mL RPMI 1640 containing a 10× antibiotic/antimycotic (penicillin/streptomycin/amphotercin B) solution to prevent overgrowth of contaminating organisms. Worm motility is observed at all initial time points, as well as 24 hour post treatment, i.e. following wash and placement in media without test compounds.

As indicated, eight concentrations and two controls are tested. The controls indicated for these tests will be a surfactant control and a media control. The protocol utilizes 5-10× of the final concentrations of test compounds to be added to the media at the time of testing.

Once the test is initiated, motility is checked at 15, 30, 60, 120, 240, and 360 minutes post-treatment. Following the last time point, the worms are removed from the treated media, rinsed and placed into untreated media. A last motility check is performed at 24 post treatment. Worms not observed to be motile are prodded with a sterile (autoclaved) wooden applicator stick to confirm lack of responsiveness.

Example 10

An exemplary test composition is used, which comprises: 7% (vol/vol) linalool; 35% (vol/vol) thymol; 4% (vol/vol) alpha-pinene; 30% (vol/vol) p-cymene; and 24% (vol/vol) soy bean oil. Test doses are: 1 mg/kg Body Weight (BW), 10 mg/kg BW, 20 mg/kg BW, are 100 mg/kg BW.

Criteria of cure used for the experiments are: (1) exposure time and efficacious dose level to produce 100% kill of *H. nana* in a minimum of 80% of infected mice (e.g., cure=0 viable worms in intestine and 0 viable eggs in stool). The short life cycle of *H. nana* can facilitate rapid prophylactic testing. *H. nana* has about a 14-day life cycle from egg infection until maturation and egg laying.

Several administration protocols are implemented to test the efficacy of the exemplary composition against infection. In a first protocol, an oral dose is administered to 5 groups of mice via gel capsule at 3 days prior to infection and daily until mice are sacrificed. In a second protocol, an oral dose is administered to 5 groups of mice via gel capsule at 3 weeks prior to infection and daily until mice are sacrificed. In a third protocol, an oral dose is administered to 5 groups of mice via gel capsule daily starting 3 weeks prior to infection, and treatment is discontinued after infection until mice are sacrificed. Control groups of mice in each of the protocols are dosed with soy bean oil only. Data from the three protocols using different mg/kg BW of the exemplary test composition are presented in Tables 5-8.

TABLE 5

| | | Number of animals carry worms | | |
| --- | --- | --- | --- | --- |
| Tested dose | Total number of animals | Positive | Negative | % Cure |
| Control Infected only | 25 | 13 (52%) | 12 | 64.0% |
| 20 mg/kg 3 wks stopped | 25 | 9 | 16 | |
| Control Infected only | 25 | 18 (72%) | 7 | 76.0% |
| 20 mg/kg 3 wks continued | 25 | 6 | 19 | |
| Control Infected only | 24 | 18 (75%) | 6 | 87.8% |
| 20 mg/kg 3 days continued | 41 | 5 | 36 | |

TABLE 6

| | % Reduction in egg production in stool at day 14 | % Reduction in ova count/worm |
| --- | --- | --- |
| Control Infected only | 0.0% | ND |
| 20 mg/kg 3 wks stopped | 76.39% | ND |
| Control Infected only | 0.0% | 0.0% |
| 20 mg/kg 3 wks continued | 93.59% | (77.85%) |
| Control Infected only | 0.0% | 0.0% |
| 20 mg/kg 3 days continued | 68.44% | (40.58%) |

TABLE 7

| Groups | % Reduction in egg production in stool | |
|---|---|---|
|  | Day 10 | Day 14 |
| Control Infected only | 0.0% | 0.0% |
| 10 mg/kg 3 days continued | 0.0% | 0.0% |
| Control* | 0.0% | 0.0% |
| 10 mg/kg 3 wks continue | 100% | 79% |
| 10 mg/kg 3 wks stopped | 85% | 43% |

TABLE 8

| Groups | % Cure | % Reduction in ova count/worm |
|---|---|---|
| Control Infected only | 0.0% | ND |
| 10 mg/kg 3 days continued | 52.0% | ND |
| Control | 0.0% | 0.0% |
| 10 mg/kg 3 wks continue | 91.3% | 95% |
| 10 mg/kg 3 wks stopped | 80% | 91% |

TABLE 9

| Treatment | N | Infection status +ve | Infection status −ve | % reduction in egg production/gm stool/mouse day 10 post infection | % reduction in egg production/gm stool/mouse day 14 post infection | Number of worms/ mouse | % reduction in Ova/worm | % Cure rate |
|---|---|---|---|---|---|---|---|---|
| Control | 23 | 12 | 11 |  |  | 5.72 ± 12 |  |  |
| 10 mg/kg 3 wks continue | 23 | 2 | 21 | 100%** | 79% | 0.4 ± 2.3 | 95% | 91.3%* |
| Control Infected only | 24 | 18 | 6 |  |  | 9.75 ± 28.2 |  |  |
| 20 mg/kg 3 days continued | 41 | 5 | 36 | ND | 68.4 | 0.07 ± 0.35 | 40.6% | 87.8%* |

Example 11

An exemplary test composition is used, which comprises: 7% (vol/vol) linalool; 35% (vol/vol) thymol; 4% (vol/vol) alpha-pinene; 30% (vol/vol) p-cymene; and 24% (vol/vol)soy bean oil.

Test groups of mice are provided for infection and treatment, each containing about 20 mice (e.g., 5 test groups×20 mice per test group=100 mice). Animals are selected and examined to ensure they are worm-free. The following test groups are designated to be infected and to received the following treatment:
  Group 1: soy bean oil carrier only;
  Group 2: 1 mg/kg body weight (BW) composition;
  Group 3: 10 mg/kg BW composition;
  Group 4: 20 mg/kg BW composition; and
  Group 5: 100 mg/kg BW composition.

An additional control group that is not infected can be provided and administered the exemplary composition.

Test groups of mice designated for infection are infected. About 150 viable eggs per mouse is determined to be useful for infecting mice such that test animal exposure to the parasite's infective stage is predictive of realistic environmental exposure.

An oral dose is administered via gel capsule to the test groups of mice at 2 days after egg shedding is observed. The oral dose is administered daily until mice are sacrificed. Half-life of doses of exemplary composition can be determined in mammalian blood to guide specification of prophylactic and therapeutic regiments.

Example 12

Resistance studies of exemplary compositions are conducted. An exemplary test composition is used, which comprises: 7% (vol/vol) linalool; 35% (vol/vol) thymol; 4% (vol/vol) alpha-pinene; 30% (vol/vol) p-cymene; and 24% (vol/vol)soy bean oil.

Test groups of mice are provided, each containing about 20 mice (e.g., 5 test groups×20 mice per test group=100 mice). Animals are selected and examined to ensure they are worm-free. The following test groups are designated to be infected and to received the following treatment:
  Group 1: soy bean oil carrier only;
  Group 2: 1 mg/kg body weight (BW) composition;
  Group 3: 10 mg/kg BW composition;
  Group 4: 20 mg/kg BW composition; and
  Group 5: 100 mg/kg BW composition.

An additional control group that is not infected can be provided and administered the exemplary composition.

Test groups of mice designated for infection are infected. About 150 viable eggs per mouse is determined to be useful for infecting mice such that test animal exposure to the parasite's infective stage is predictive of realistic environmental exposure. Target DNA from the eggs used for the initial infection is sequenced prior to treatment with exemplary compositions, for use as a control sequence.

An oral dose is administered via gel capsule to the test groups of mice at 2 days after egg shedding observed. The oral dose is administered daily until the mice are sacrificed. The viable eggs are counted and collected. The collected viable eggs are used to re-infect the previously uninfected animal test group, which are then treated with the exemplary composition as before. The step is repeated, for a total of three counts and collections of viable eggs. Following the third count and collection of viable eggs, the viable egg target DNA is sequenced.

The parasite is assumed to have gone through three reproductive cycles. The control unexposed DNA sequence can be compared to the target DNA sequence obtained from eggs after the third cycle, having three successive exposures to the exemplary treatment compositions. Resistance is determined by considering: no change in exposed target DNA sequence vs. control target DNA sequence results in one or more amino acid changes.

Example 13

Safety studies are of exemplary compositions are conducted. Safety studies include acute toxicity tests (range finding), in vitro genetic toxicology studies, and sub-chronic rodent toxicity study (90-day) conducted under Good Laboratory Practices (GLP).

Animals are exposed to daily doses of the therapeutic compositions being tested. For example, an exemplary test composition can be used, which comprises: 7% (vol/vol) linalool; 35% (vol/vol) thymol; 4% (vol/vol) alpha-pinene; 30% (vol/vol) p-cymene; and 24% (vol/vol) soy bean oil. The following test groups are designated to receive the following treatment:

Group 1: soy bean oil carrier only;
Group 2: 0.07 g/kg body weight (BW) per day;
Group 3: 0.7 g/kg BW per day; and
Group 4: 7 g/kg BW per day.

All appropriate observational and clinical tests (including histopathology) are performed to assess any treatment-related effects. Safety measures (see Table 10) are made at 100× the efficacious dose using a prophylactic efficacy protocol. For example, if the efficacious dose is 10 mg/kg, the safety test dose is 1 g/kg.

TABLE 10

| Safety Measures | Sample size (# of mice) | Key Metric |
|---|---|---|
| changes in body weight | 20-40 | less than 11% body weight change, test vs. control |
| changes in water intake | 20-40 | less than 11% differential, test vs. control |
| changes in food intake | 20-40 | less than 11% differential, test vs. control |
| red blood cell count | 20-40 | no significant difference vs. control or within normal range |
| white blood cell count | 20-40 | no significant difference vs. control or within normal range |
| hemoglobin | 20-40 | no significant difference vs control or within normal range |
| sGOT (liver function) | 20-40 | no significant difference vs. control or within normal range |
| sGPT (liver function) | 20-40 | no significant difference vs. control or within normal range |
| creatinine | 20-40 | no significant difference vs. control or within normal range |
| fecal matter consistency | 20-40 | no significant difference vs. control or within normal range |

Relative palatability of exemplary compositions is also tested. Synergistic combinations of compounds can be designed to favor compounds with preferred palatability.

Example 14

A receptor gene encoding the Tyramine receptor (TyrR) has been isolated from the American cockroach, fruit fly, mosquito, and other organisms. The present subject matter provides methods of utilizing the TyrR protein expressed in cells to screen for compounds useful for treating parasitic infections.

In the present Example, the genes encoding TyrR were incorporated into model cells in culture that mimic receptors in insects. The screening process uses the cultured cells in combination with $[Ca^{2+}]i$ and $[cAMP]i$ measuring assays to quantitatively determine effectiveness of test compound to treat parasitic infections. The screening process allows for identification of compounds that produce highly efficacious anti-parasitic compositions.

The assay steps are as follows. A cell expressing a tyramine receptor is contacted with a test compound and the receptor binding affinity of the test compound is measured. cAMP and/or $Ca^{2+}$ levels within the cell are also monitored and any changes from contacting the test compound with the cell are noted for each compound tested. A test compound is identified as a potential therapeutic compound if it exhibits a high receptor binding affinity for the tyramine receptor as well as an ability to effect change in cAMP and/or $Ca^{2+}$ levels within the cell. A test compound is also identified as a potential therapeutic compound if it exhibits a low receptor binding affinity for the tyramine receptor as well as an ability to effect change in cAMP and/or $Ca^{2+}$ levels within the cell. A composition for use in treating a parasitic formulation can then be selected that includes a plurality of the identified compounds. In particular, the composition can comprise at least one compound identified as having a high receptor binding affinity for the tyramine receptor as well as an ability to effect change in cAMP and/or $Ca^{2+}$ levels within the cell and at least one additional compound identified as having a low receptor binding affinity for the tyramine receptor as well as an ability to effect change in cAMP and/or $Ca^{2+}$ levels within the cell.

Table 11 lists compounds tested with the present screening method and the determined capacity of each compound to bind the tyramine receptor, effect intracellular $Ca^{2+}$, and effect intracellular cAMP. These results can then be utilized to select a composition comprising two or more of the tested compounds with desirable characteristics. For example, p-cymene and linalool can be select to include in a composition for treating parasitic infections according to the screening method criteria since p-cymene exihibits low tyramine receptor binding affinity, linalool exhibits high tyramine receptor binding affinity, and both compounds effect change in cAMP and/or Ca2+ levels. Similarly, p-cymene and thymol can be select to include in a composition for treating parasitic infections according to the screening method criteria since p-cymene exihibits low tyramine receptor binding affinity, thymol exhibits high tyramine receptor binding affinity, and both compounds effect change in cAMP and/or Ca2+ levels. Further, compositions for treating parasitic infections can be formulated that include more than two compounds, such as for example a composition that includes alpha-pinene, p-cymene, linalool, thymol, and soybean oil. It can be preferable to formulate a composition that displays an anti-parasitic effect exceeding the anti-parasitic effect of any of the compounds when used alone.

TABLE 11

| Compound | Tyramine Receptor Binding Affinity (High or Low) | Effects Intracellular $Ca^{2+}$ (Yes or No) | Effects Intracellular cAMP (Yes or No) |
|---|---|---|---|
| alpha-pinene | Low | No | No |
| anethole | Low | Yes | Yes |

TABLE 11-continued

| Compound | Tyramine Receptor Binding Affinity (High or Low) | Effects Intracellular $Ca^{2+}$ (Yes or No) | Effects Intracellular cAMP (Yes or No) |
|---|---|---|---|
| benzyl alcohol | Low | No | Yes |
| black seed oil | High | Yes | Yes |
| cedar oil | Low | Yes | Yes |
| cineol | Low | Yes | Yes |
| cinnamon oil | Low | No | No |
| cinnamyl alcohol | Low | Yes | No |
| citronella oil | Low | No | Yes |
| clove oil | Low | Yes | Yes |
| p-cymene | Low | Yes | Yes |
| d-limonene | High | Yes | Yes |
| Eugenol | Low | Yes | No |
| garlic oil | Low | Yes | Yes |
| lemon oil | Low | No | No |
| lemongrass oil | Low | No | No |
| lilac flower oil | High | Yes | Yes |
| lime oil | Low | Yes | Yes |
| d-limonene | Low | Yes | No |
| linalool | High | Yes | No |
| linseed oil | Low | No | No |
| oil of pennyroyal | Low | Yes | Yes |
| orange sweet oil | Low | Yes | No |
| peppermint oil | Low | No | Yes |
| phenethyl proprionate | Low | No | Yes |
| pine oil | Low | No | No |
| rosemary oil | Low | No | No |
| sodium lauryl sulfate | Low | No | No |
| soybean oil | Low | No | No |
| thyme oil | High | Yes | Yes |
| thymol | High | Yes | No |
| vanillin | Low | Yes | No |
| white mineral oil | Low | Yes | Yes |
| geraniol | High | Yes | Yes |
| tetrahydrolinalool | High | Yes | Yes |

What is claimed is:

1. A method of treating a parasitic infection in a mammal or bird in need thereof, comprising administering to the mammal or bird a composition which comprises between 9.92% and 37.2% isolated para-cymene, between 6.36% and 9.8% isolated linalool, between 3.2% and 4.07% isolated alpha-pinene and between 13.5% and 46.2% isolated thymol wherein the composition is encapsulated or microencapsulated with an outer shell material.

2. The method of claim 1, wherein the parasitic infection is by a parasite selected from the group consisting of a protozoan parasite, and a helminthic parasite.

3. The method of claim 2, wherein the parasite is selected from the group consisting of Entamoeba hystolytica, Giardia lamblia, Cryptosporidium muris, Trypanosomatida gambiense, Trypanosomatida rhodesiense, Trypanosomatida crusi, Leishmania mexicana, Leishmania braziliensis, Leishmania tropica, Leishmania donovani, Toxoplasma gondii, Plasmodium vivax, Plasmodium ovale, Plasmodium malariae, Plasmodium falciparum, Trichomonas vaginalis, Histomonas meleagridis, Trichuris trichiura, Ascaris lumbricoides, Enterobius vermicularis, Ancylostoma duodenale, Necator americanus, Strongyloides stercoralis, Wuchereria bancrofti, Dracunculus medinensis, Schistosoma mansoni, Schistosoma haematobium, Schistosoma japonicum, Fasciola hepatica, Fasciola gigantica, Heterophyes heterophyes, Paragonimus westermani, Taenia solium, Taenia saginata, Hymenolepis nana, and Echinococcus granulosus.

4. The method of claim 1, wherein the mammal is selected from the group consisting of a human, a ruminant, an ungulate, a swine, poultry, a horse, and a carnivore.

5. The method of claim 1, wherein the composition comprises a carrier.

6. The method of claim 5, wherein the carrier is a food product.

7. The method of claim 1, wherein the composition comprises about 28.39% by weight isolated para-cymene, about 6.6% by weight isolated linalool, about 3.8% by weight isolated alpha-pinene, and about 37.2% by weight isolated thymol.

* * * * *